United States Patent [19]

Helgstrand et al.

[11] Patent Number: 4,591,583
[45] Date of Patent: May 27, 1986

[54] PHOSPHONOFORMIC ACID ESTERS AND PHARMACEUTICAL COMPOSITIONS CONTAINING SAME

[75] Inventors: Åke J. E. Helgstrand; Karl N. Johansson, both of Enhörna; Alfons Misiorny, Bandhagen; Jan O. Norén, Grödinge; Göran B. Stening, Södertälje, all of Sweden

[73] Assignee: Astra Lakemedel Aktiebolag, Sodertalje, Sweden

[21] Appl. No.: 450,656

[22] Filed: Dec. 17, 1982

Related U.S. Application Data

[60] Division of Ser. No. 93,167, Nov. 13, 1979, Pat. No. 4,386,081, which is a continuation-in-part of Ser. No. 971,896, Dec. 21, 1978, abandoned.

[30] Foreign Application Priority Data

Dec. 22, 1977 [GB] United Kingdom ............... 53580/77
Dec. 22, 1977 [GB] United Kingdom ............... 53581/77
Dec. 22, 1977 [GB] United Kingdom ............... 53582/77
Dec. 22, 1977 [GB] United Kingdom ............... 53583/77
Jul. 3, 1978 [GB] United Kingdom ............... 28548/78
Jul. 3, 1978 [GB] United Kingdom ............... 28552/78
Jul. 3, 1978 [GB] United Kingdom ............... 28553/78
Jul. 3, 1978 [GB] United Kingdom ............... 28555/78

[51] Int. Cl.⁴ ............................................. A61K 31/66
[52] U.S. Cl. .................................................. 514/120
[58] Field of Search ........................ 424/212; 514/120

[56] References Cited

FOREIGN PATENT DOCUMENTS 2238432 3/1980 France.

OTHER PUBLICATIONS

Alenius, et al., "Therapeutic Effect of Trisodium Phosphonoformate on Cutaneus Herpes Virus Infection in Guinea Pigs," *Antimicrobial Agents and Chemotherapy*, Sep. 1978.
Palmer, et al., "Disodium Phosphonoacetate in Cream Base as a Possible Topical Treatment for Skin Lesions at Herpes Simplex Virus in Cebus Monkeys," *Antimicrobial Agents and Chemotherapy*, Oct. 1977.
Chemical Abstracts, vol. 50, No. 2, 794d, (1956).
Galasso, "An Assessment of Antiviral Drugs for the Management of Infectious Diseases in Humans," *Antiviral Research*, 1 (1981), 73–96.
Kern et al., "Treatment of Experimental Herpesvirus Infections with Phosphonoformate and Some Comparisons with Phosphonoacetate", *Antimicrobial Agents and Chemotherapy*, 14 (Dec. 1978), 817–823.

*Primary Examiner*—Jerome D. Goldberg
*Attorney, Agent, or Firm*—Brumbaugh, Graves, Donohue & Raymond

[57] ABSTRACT

A pharmaceutical preparation containing as active ingredient a compound of the formula

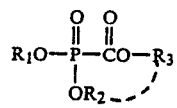

I wherein $R_1$ and $R_2$ are the same or different, and each is selected from the group consisting of hydrogen, alkyl groups containing 1-6 carbon atoms; cycloalkyl groups containing 3-6 carbon atoms; cycloalkyl-alkyl groups containing 4-6 carbon atoms; 1-adamantyl; 2-adamantyl, benzyl; and phenyl groups of the formula

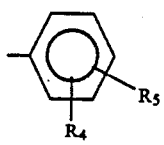

II wherein $R_4$ and $R_5$ are the same or different and each is selected from the group consisting of hydrogen, halogen, alkyl having 1, 2, or 3 carbon atoms, alkoxy having 1, 2, or 3 carbon atoms, alkoxycarbonyl having 2-7 carbon atoms and alkylcarbonyl groups having 2-7 carbon atoms; or $R_4$ and $R_5$ together form a straight saturated alkylene chain having 3 or 4 carbon atoms and being bound to adjacent positions, i.e. 2,3- or 3,4- in the phenyl ring; and $R_3$ is selected from the group consisting of hydrogen, alkyl groups containing 1-8 carbon atoms; cycloalkyl groups containing 3-8 carbon atoms; cycloalkyl-alkyl groups containing 4-8 carbon atoms; 1-adamantyl; 2-adamantyl; benzyl; and phenyl groups of the formula

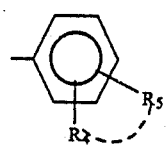

wherein $R_4$ and $R_5$ have the meaning given above; provided that at least one of the groups $R_1$, $R_2$ and $R_3$ is alkyl, cycloalkyl, or cycloalkyl-alkyl as defined above, or 1-adamantyl, 2-adamantyl, or benzyl; and provided that when $R_3$ is H, then one of $R_1$ and $R_2$ is alkyl, cycloalkyl, or cycloalkyl-alkyl as defined above, or 1-adamantyl, 2-adamantyl, or benzyl and the other of $R_1$ and $R_2$ is H; or a physiologically acceptable salt or an optical isomer thereof; novel compounds within formula I, methods for their preparation and their medicinal use.

7 Claims, No Drawings

PHOSPHONOFORMIC ACID ESTERS AND PHARMACEUTICAL COMPOSITIONS CONTAINING SAME

This application is a divisional of Application Ser. No. 093,167, filed on Nov. 13, 1979, now U.S. Pat. No. 4,386,081, which is a continuation-in-part of application Ser. No. 971,896, filed on Dec. 21, 1978, now abandoned.

FIELD OF THE INVENTION

The present invention relates to novel pharmaceutical compositions and to a novel method for selectively combating viruses, such as herpes viruses, influenza viruses, etc., which can cause various diseases in animals including man. Such diseases include common infections. In those cases where, the active ingredient in the composition is a novel compound, the invention also comprises the novel compounds per se and processes for their preparation.

BACKGROUND OF THE INVENTION

The effects of viruses on bodily functions is the end result of changes occuring at the cellular and subcellular levels. The pathogenic changes at the cellular level are different for different combinations of viruses and host cells.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpesvirus group. Other important viral diseases are influenza A and B which are caused by influenza A and B virus respectively. Another important common viral disease is viral hepatitis and especially hepatitis B virus infections are widely spread. Effective and selective antiviral agents are needed for the treatment of these diseases.

A most important common feature of the interaction between viruses and cells is the replication or transcription of the specific viral genetic information carried by viral nucleic acids. These viral nucleic acids are of two kinds, deoxyribonucleic acids (DNA) or ribonucleic acids (RNA). The primary genetic information of the cell is carried by cell DNA. DNA and RNA synthesis involves complex enzymes called DNA and RNA polymerases respectively. The genetic information is transferred to the new nucleic acid from a template nucleic acid. There are four general ways in which these nucleic acids can be replicated or transcribed.

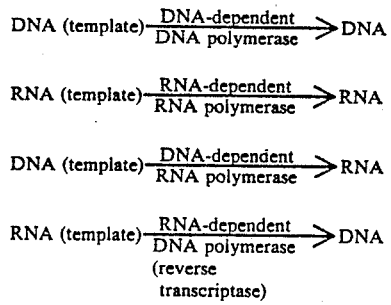

Processes 1 and 3 are used by cells. DNA viruses such as herpesviruses also use process 1 but the enzyme is different from that of the cell. RNA viruses such as influenza virus use process 2. There is a need for an effective antiviral agent preferably having a selective inhibiting effect on a specific viral function of the virus to be combated. It is, therefore, a general object of the present invention to provide a novel method for combating virus infections using an antiviral agent which exerts a selective inhibiting effect on viral functions but which exerts only a negligible inhibiting effect on functions of the host cells.

THE INVENTION

It has been found according to the present invention that the compounds of the formula

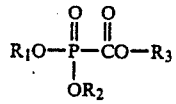

I wherein $R_1$ and $R_2$ are the same or different, and each is selected from the group consisting of hydrogen, alkyl groups containing 1–6 carbon atoms; cycloalkyl groups containing 3–6 carbon atoms: cycloalkyl-alkyl groups containing 4–8 carbon atoms; 1-adamantyl; 2-adamantyl, benzyl; and phenyl groups of the formula

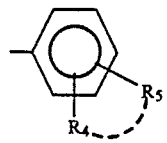

II wherein $R_4$ and $R_5$ are the same or different and each is selected from the group consisting of hydrogen, halogen, alkyl having 1, 2, or 3 carbon atoms, alkoxy having 1, 2 or 3 carbon atoms, alkoxycarbonyl having 2–7 carbon atoms and alkylcarbonyl groups having 2–7 carbon atoms; or $R_4$ and $R_5$ together form a straight saturated alkylene chain having 3 or 4 carbon atoms and being bound to adjacent positions, i.e. 2,3- or 3,4- in the phenyl ring; and $R_3$ is selected from the group consisting of hydrogen, alkyl groups containing 1–8 carbon atoms; cycloalkyl groups containing 3–8 carbon atoms; cycloalkyl-alkyl groups containing 4–8 carbon atoms; 1-adamantyl; 2-adamantanyl; benzyl; and phenyl groups of the formula

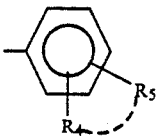

wherein $R_4$ and $R_5$ have the meaning given above; provided that at least one of the groups $R_1$, $R_2$ and $R_3$ is alkyl, cycloalkyl, or cycloalkyl-alkyl as defined above, or 1-adamantyl, 2-adamantyl, or benzyl; and provided that when $R_3$ is H, then one of $R_1$ and $R_2$ is alkyl, cycloalkyl, or cycloalkyl-alkyl as defined above, or 1-adamantyl, 2-adamantyl, or benzyl and the other of $R_1$ and $R_2$ is H; and physiologically acceptable salts thereof, inhibit certain viral functions including the multiplication of viruses.

It is understood that the reference to "physiologically acceptable salts" of the compounds of the formula I in the present specification and claims relates only to such compounds which can form salts. Compounds wherein at least one of $R_1$, $R_2$ and $R_3$ is hydrogen can form salts. Compounds wherein all of $R_1$, $R_2$ and $R_3$ are different from hydrogen do not form salts.

Since the compounds of the formula I, when $R_1$ and $R_2$ are different, contain an asymmetric center, they exist in the form of optically active forms, and can be resolved into their optical antipodes by known methods.

In this specification, the compounds of the invention are named as derivatives of the compound hydroxycarbonylphosphonic acid, which compound also is known under the name phosphonoformic acid.

The two provisions in the definition of the compounds of the invention mean that the radicals $R_1$, $R_2$ and $R_3$ in formula I can be combined as illustrated in the following tabulation. It is understood that $R_1$ and $R_2$, which are the same or different, are considered as equivalent and interchangeable in the table below.

| $R_1$ | $R_2$ | $R_3$ |
|---|---|---|
| alkyl, cycloalkyl, cycloalkyl-alkyl, 1-adamantyl, 2-adamantyl, benzyl | H | H |
| alkyl, cycloalkyl, cycloalkyl-alkyl, 1-adamantyl, 2-adamantyl, benzyl, phenyl groups of formula II | H | alkyl, cycloalkyl, cycloalkyl-alkyl, 1-adamantyl, 2-adamantyl, benzyl, phenyl groups of formula II |
| alkyl, cycloalkyl, cycloalkyl-alkyl, 1-adamantyl, 2-adamantyl, benzyl | H | phenyl groups of formula II |
| phenyl groups of formula II | H | alkyl, cycloalkyl, cycloalkyl-alkyl, 1-adamantyl, 2-adamantyl, benzyl |
| alkyl, cycloalkyl, cycloalkyl-alkyl, 1-adamantyl, 2-adamantyl, benzyl, phenyl groups of formula II | alkyl, cycloalkyl, cycloalkyl-alkyl, 1-adamantyl, 2-adamantyl, benzyl, phenyl groups of formula II | phenyl groups of formula II |
| alkyl, cycloalkyl, cycloalkyl-alkyl, 1-adamantyl, 2-adamantyl, benzyl, phenyl groups of formula II | phenyl groups of formula II | alkyl, cycloalkyl, cycloalkyl-alkyl, 1-adamantyl, 2-adamantyl, benzyl, phenyl groups of formula II |
| alkyl, cycloalkyl, cycloalkyl-alkyl, 1-adamantyl, 2-adamantyl, benzyl | phenyl groups of formula II | phenyl groups of formula II |
| alkyl, cycloalkyl, cycloalkyl-alkyl, 1-adamantyl, 2-adamantyl, benzyl, phenyl groups of formula II | alkyl, cycloalkyl, cycloalkyl-alkyl, 1-adamantyl, 2-adamantyl, benzyl, phenyl groups of formula II | alkyl, cycloalkyl, cycloalkyl-alkyl, 1-adamantyl, 2-adamantyl, benzyl, phenyl groups of formula II |
| H | H | alkyl, cycloalkyl, cycloalkyl-alkyl, 1-adamantyl, 2-adamantyl, benzyl |

The first provision means that in the above table, combinations wherein $R_1$, $R_2$ and $R_3$ all are H or phenyl groups of formula II are excluded.

The compounds of the formula I and physiologically acceptable salts thereof are useful in therapeutic and/or prophylactic treatment of viral diseases.

PRIOR ART

The compounds of the formula I are esters of phosphonoformic acid. Various esters of phosphonoformic acid are described in for example U.S. Pat. Nos. 3,943,201, 3,155,597, 3,533,995, and in Chem. Ber. 57 p1023 (1924), Chem. Ber. 60B, p291 (1927), and in Chem. Pharm. Bull. 21 (5), p1160 (1973). However, these esters have not been suggested for any pharmacological use.

DETAILED DESCRIPTION OF THE INVENTION

The present invention provides

A. A method for treatment of diseases caused by viruses in animals including man, comprising administering to an animal so infected to therapeutically effective amount of a compound of the formula I or a physiologically acceptable salt thereof.

B. A method for the treatment of diseases caused by viruses in animals including man, by inhibiting the activity of viral polymerase, characterized by administering to an animal so infected a compound of the formula I or a physiologically acceptable salt thereof in an amount effective for inhibiting the activity of said viral polymerase.

C. A method for inhibiting the multiplication of virus, in particular herpesviruses, influenza virus and hepatitis B virus, and retroviruses in animals including man, by administering to an animal in need of such treatment a compound of the formula I or a physiologically acceptable salt thereof in an amount sufficient for inhibiting said multiplication.

D. A method for inhibiting the growth of virus-transformed cells in animals including man, characterized by administering to an animal in need of such treatment a compound of the formula I or a physiologically acceptable salt thereof in an amount sufficient for inhibiting said growth.

The invention also relates to the use of a compound of the formula I or a physiologically acceptable salt thereof, in each of the above given methods, A, B, C, D, E, F, G, H, and I. For example, the invention relates to the use of a compound of the formula I or a physiologically acceptable salt thereof, for (a) inhibiting the replication of virus in animals including man, in particular herpesvirus, influenza virus and hepatitis B viruses; and (b) for inhibiting the growth of virus-transformed cells in animals including man.

Furthermore, the invention provides pharmaceutical preparations comprising as active ingredient a compound of the formula I or a physiologically acceptable salt thereof, optionally in association with a pharmaceutically acceptable carrier. The invention also encompasses a process for the preparation of a medicine having antiviral acitivity, characterized in that a compound of the formula I or a physiologically acceptable salt thereof is brought into an administration form suitable for therapeutical purposes, and the shaped medicine obtained by such process.

Most of the compounds within the formula I are novel compounds, and in those cases where the active ingredient in the composition is such a compound, the invention also comprises the novel compounds per se.

Compounds included in formula I wherein $R_1$, $R_2$ and $R_3$ are combined as follows are generically disclosed in the prior art:

| $R_1$ | $R_2$ | $R_3$ |
|---|---|---|
| H | alkyl | alkyl |
| H | alkyl | benzyl |
| H | benzyl | alkyl |
| H | benzyl | benzyl |
| H | H | alkyl |
| H | H | benzyl |
| alkyl | alkyl | alkyl |
| alkyl | alkyl | phenyl |
| alkyl | alkyl | phenyl substituted with alkyl having 1–3 carbon atoms. |

The invention includes the compounds per se of formula I excluding the groups of compounds given in the above table.

In tables below, compounds of the formula I which are known from the prior art are indicated. The invention includes within its scope those compounds per se which are included in formula I and which are not known in the prior art. In particular compounds wherein $R_1$, $R_2$ or $R_3$ are 1-adamantyl, 2-adamantyl, or phenyl groups of the formula II wherein the radicals $R_4$ and $R_5$ are the same or different and selected from the groups consisting of halogen, alkoxy having 1–3 carbon atoms, alkoxycarbonyl having 2–3 carbon atoms, and alkylcarbonyl having 2–7 carbon atoms, or wherein $R_4$ and $R_5$ together form a straight saturated alkylene chain having 3 or 4 carbon atoms and being bound to adjacent positions i.e. 2,3- or 3,4- in the phenyl ring, are novel. Further groups of novel compounds, which also are included in the scope of the invention, are indicated in the preferred groups of radicals which are enumerated elsewhere in this specification. Those individual compounds which are enumerated in tables below, or which are exemplified in working examples, and which are not indicated as known in the art, are believed to be novel and included within the scope of the invention.

The compounds of the formula I may be hydrolyzed in vivo to give phosphonoformic acid or ionized forms thereof, which are antiviral agents. In a more generalized aspect the invention includes within its scope the use of all physiologically acceptable compounds (including physiologically acceptable salts thereof) of the formula I, wherein $R_1$, $R_2$ and $R_3$, when they are different from H, are any pharmaceutically acceptable organic group, which by in vivo hydrolysis is capable of forming phosphonoformic acid or a physiologically acceptable salt thereof in the animal body (i.e. bioprecursors to phosphonoformic acid) for the treatment of virus infections and related ailments, as previously described, in animals including man, and pharmaceutical compositions containing such compounds.

Phosphonoformic acid and physiologically acceptable salts thereof inhibit viral functions such as polymerases including reverse transcriptase and virus multiplication, and have effects on virus infections in animal models. The antiviral effects of trisodium phosphonoformate is described by Helgstrand et. al. Science 201, 819 (1978).

An important aspect of the invention is that the radicals $R_1$, $R_2$ and $R_3$ in formula I can be chosen in such a way that the compounds of formula I and physiologically acceptable salts thereof possess more favourable pharmacokinetic properties than phosphonoformic acid and physiologically acceptable salts thereof. Such favourable pharmacokinetic properties include better tissue penetration, better oral absorption and prolonged activity.

Although the present invention relates broadly to a novel method for selectively combating viral diseases in animals and man, and pharmaceutical preparations to be used in such treatment, it will be particularly useful in the treatment of herpesvirus infections, influenza virus infections, hepatitis B virus infections.

An especially important area of use for the compositions of the present invention is in the treatment of herpes virus infections. Among the herpesviruses may be mentioned Herpes simplex type 1 and 2, varicella (Herpes zoster), virus causing infectious mononucleosis (i.e. Epstein-Barr virus), and cytomegalovirus. Important diseases caused by herpes viruses are herpes dermatitis, (including herpes labialis), herpes genitalis, herpes keratitis and herpes encephalitis. An other important area of use for the compositions of the present invention is in the treatment of infections caused by orthomyxoviruses, i.e. influenza viruses of type A and type B. A further area of use is the treatment of infections caused by viruses such as hepatitis virus A and hepatitis virus B, papillomaviruses, adenoviruses and poxviruses.

Other possible areas of use for the compositions of the present invention are in the treatment of infections caused by picornaviruses, togaviruses including arboviruses, retroviruses (e.g. leucoviruses), arenaviruses, coronaviruses, rhabdoviruses, paramyxoviruses, hepatitis non A and non B virus, iridoviruses, papovaviruses, parvoviruses, reoviruses, and bunyaviruses.

Illustrative examples of the meanings of the radicals $R_1$, $R_2$ and $R_3$ in the formula I above are:

alkyl:

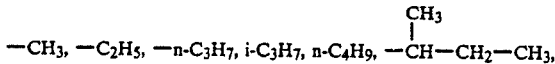

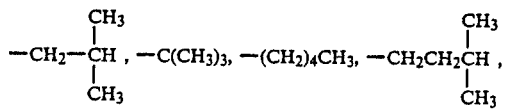

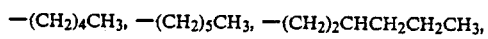

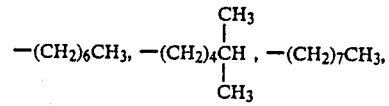

cycloalkyl:

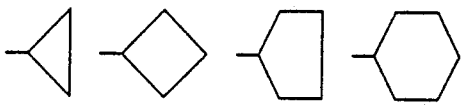

cycloalkyl-alkyl:

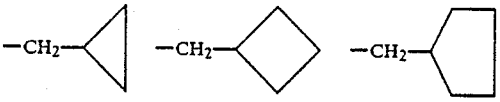

-continued

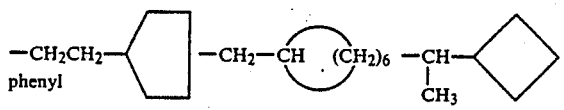

substituted phenyl:

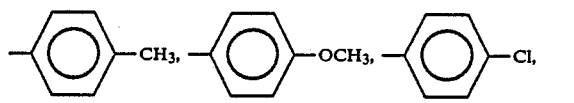

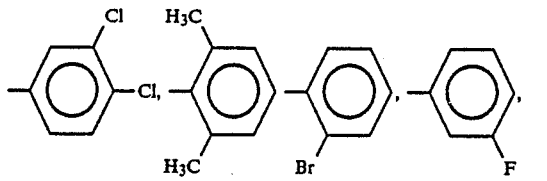

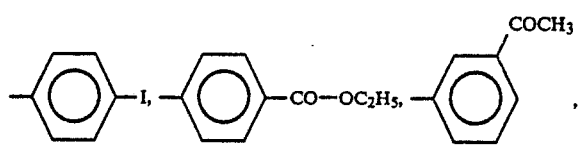

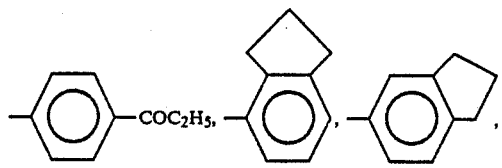

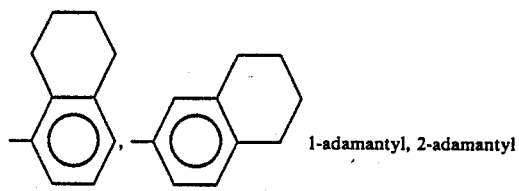, 1-adamantyl, 2-adamantyl

The above illustrative examples are intended to illustrate the meanings of all the radicals $R_1$, $R_2$, and $R_3$ within the boundaries with regard to number of carbon atoms which are prescribed for each radical.

Preferred groups of the radicals $R_1$ and $R_2$ are:
1. The group consisting of straight and branched alkyl groups containing 1–6 carbon atoms, phenyl, and benzyl;
2. The group consisting of straight and branched alkyl groups containing 1–4 carbon atoms; phenyl, and benzyl;
3. The group consisting of straight and branched alkyl groups containing 1–6 carbon atoms;
4. The group consisting of straight and branched alkyl groups containing 1–4 carbon atoms, that is methyl, ethyl, n-propyl, i-propyl, n-butyl, i-butyl, sec-butyl and t-butyl.
5. Phenyl
6. Benzyl
7. 1-adamantyl (novel compounds);
8. 2-adamantyl (novel compounds);
9. monosubstituted phenyl groups: (novel compounds);
10. disubstituted phenyl groups (novel compounds);
11. mono-alkyl substituted phenyl groups (novel compounds)
12. mono-halogen substituted phenyl groups (novel compounds);
13. mono-alkoxy substituted phenyl groups (novel compounds);
14. mono-alkoxycarbonyl substituted phenyl groups (novel compounds);
15. di-alkyl substituted phenyl groups (novel compounds);
16. di-halogen substituted phenyl groups (novel compounds);
17. di-alkoxy substituted phenyl groups (novel compounds);
18. phenyl groups of the formula

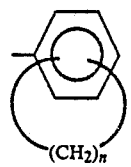

wherein n is 3 or 4 and wherein the alkylene chain is bound to adjacent positions, i.e. 2,3- or 3,4- in the phenyl ring (novel compounds).
19. mono-alkylcarbonyl substituted phenyl groups (novel compounds)
20. cycloalkyl and cycloalkyl-alkyl groups (novel compounds)

Particularly preferred groups of the radicals $R_1$ and $R_2$ are unsubstituted, monosubstituted and disubstituted phenyl groups within the above formula

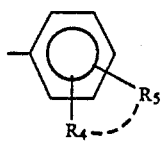

wherein $R_4$ and $R_5$ have the meanings given above.

In a preferred embodiment, $R_1$ and $R_2$ have the same meaning.

Preferred groups of the radical $R_3$ are:
1. The groups consisting of straight and branched alkyl groups containing 1–8 carbon atoms; phenyl; and benzyl;
2. The group consisting of straight and branched alkyl groups containing 1–4 carbon atoms; phenyl; and benzyl;
3. The group consisting of straight and branched alkyl groups containing 1–8 carbon atoms;
4. The group consisting of straight and branched alkyl groups containing 1–4 carbon atoms, that is methyl, ethyl, n-propyl, i-propyl, n-butyl, i-butyl, sec-butyl and t-butyl.
5. Phenyl
6. Benzyl
7. 1-adamantyl (novel compounds);
8. 2-adamantyl (novel compounds);
9. monosubstituted phenyl groups;
10. disubstituted phenyl groups (novel compounds);
11. mono-alkyl substituted phenyl groups;
12. mono-halogen substituted phenyl groups (novel compounds);
13. mono-alkoxy substituted phenyl groups (novel compounds);

14. mono-alkoxycarbonyl substituted phenyl groups (novel compounds);

15. di-alkyl substituted phenyl groups (novel compounds);

16. di-halogen substituted phenyl groups (novel compounds);

17. di-alkoxy substituted phenyl groups (novel compounds);

18. phenyl groups of the formula

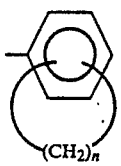

wherein n is 3 or 4 and wherein the alkylene chain is bound to adjacent positions, i.e. 2,3- or 3,4- in the phenyl ring (novel compounds).

19. mono-alkylcarbonyl substituted phenyl groups (novel compounds);

20. cycloalkyl and cycloalkyl-alkyl groups (novel compounds);

Particularly preferred groups of the radical $R_3$ are unsubstituted, monosubstituted and disubstituted phenyl groups within the above formula

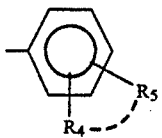

wherein $R_4$ and $R_5$ have the meanings given above.

Preferred combinations of $R_1$, $R_2$, and $R_3$ are:

1. $R_1$ and $R_2$ are selected from the group consisting of straight and branched alkyl groups containing 1–6 carbon atoms, phenyl, and benzyl; and $R_3$ is selected from the group consisting of straight and branched alkyl groups containing 1–6 carbon atoms, phenyl, and benzyl;

2. $R_1$, $R_2$, and $R_3$ are selected from the group consisting of straight and branched alkyl groups containing 1–4 carbon atoms; phenyl; and benzyl;

3. $R_1$ and $R_2$ are selected from the group consisting of straight and branched alkyl groups containing 1–6 carbon atoms; and $R_3$ is selected from the group consisting of straight and branched alkyl groups containing 1–8 carbon atoms;

4. $R_1$, $R_2$, and $R_3$ are selected from the group consisting of straight and branched alkyl groups containing 1–4 carbon atoms;

5. $R_1$, $R_2$, and $R_3$ are benzyl (novel compound);

6. in each of the groups 1–4 above, $R_1$ having the same meaning as $R_2$;

7. $R_1$ and $R_2$ are selected from the group consisting of alkyl groups containing 1–4 carbon atoms and $R_3$ is selected from the group consisting of an unsubstituted, monosubstituted or disubstituted phenyl group within the formula

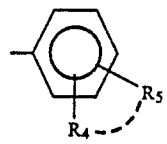

wherein $R_4$ and $R_5$ have the meanings given above (novel compounds except where $R_3$ is mono-alkyl substituted phenyl);

8. $R_1$ is an alkyl group containing 1–4 carbon atoms, $R_2$ and $R_3$ are the same or different and are selected from the group consisting of unsubstituted, monosubstituted or disubstituted phenyl groups within the formula

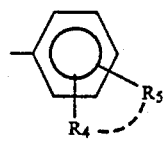

wherein $R_4$ and $R_5$ have the meanings given above (novel compounds);

9. $R_1$ and $R_2$ are the same or different and are selected from the group consisting of an unsubstituted, monosubstituted or disubstituted phenyl group within the formula

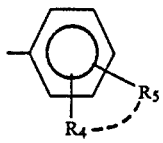

wherein $R_4$ and $R_5$ have the meanings given above, and $R_3$ is an alkyl group containing 1–4 carbon atoms (novel compounds);

10. $R_1$ and $R_2$ are the same or different and are selected from the group consisting of alkyl groups containing 1–4 carbon atoms, and $R_3$ is selected from the group consisting of 1-adamantyl and 2-adamantyl (novel compounds);

11. $R_1$, $R_2$, and $R_3$ are selected from the group consisting of straight and branched alkyl groups containing 1–4 carbon atoms, benzyl, unsubstituted, monosubstituted or disubstituted phenyl groups within the formula

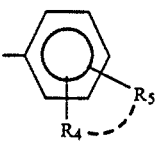

wherein $R_4$ and $R_5$ have the meanings given above; 1-adamantyl; and 2-adamantyl, whereby at least one of the groups $R_1$, $R_2$, and $R_3$ is not alkyl or benzyl.

12. $R_1$ and $R_2$ are selected from the group consisting of straight and branched alkyl groups containing 1–4 carbon atoms; and unsubstituted, monosubstituted or disubstituted phenyl groups with the formula

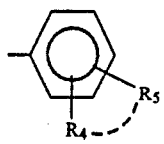

wherein $R_4$ and $R_5$ have the meanings given above; and $R_3$ is selected from the group consisting of 1-adamantyl and 2-adamantyl (novel compounds);

13. $R_1$ and $R_2$ are selected from the group consisting of straight and branched alkyl groups containing 1–4 carbon atoms; and unsubstituted, monosubstituted or disubstituted phenyl groups within the formula

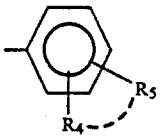

wherein $R_4$ and $R_5$ have the meanings given above; and $R_3$ is benzyl;

14. in each of the groups 7, 9, 10, 11, 12, and 13 above, $R_1$ having the same meaning as $R_2$.

15. $R_1$ and $R_2$ are hydrogen and $R_3$ is selected from the group consisting of straight and branched alkyl groups containing 1–8 carbon atoms; and benzyl;

16. $R_1$ and $R_2$ are hydrogen and $R_3$ is selected from the group consisting of straight and branched alkyl groups containing 1–4 carbon atoms; and benzyl;

17. $R_1$ and $R_2$ are hydrogen and $R_3$ is selected from the group consisting of straight and branched alkyl groups containing 1–8 carbon atoms;

18. $R_1$ and $R_2$ are hydrogen and $R_3$ is selected from the group consisting of straight and branched alkyl groups containing 1–4 carbon atoms, that is methyl, ethyl, n-propyl, i-propyl, n-butyl, i-butyl, sec-butyl, and t-butyl;

19. $R_1$ and $R_2$ are hydrogen and $R_3$ is benzyl;

20. $R_1$ and $R_2$ are hydrogen and $R_3$ is 1-adamantyl (novel compound);

21. $R_1$ and $R_2$ are hydrogen and $R_3$ is 2-adamantyl (novel compound);

22. $R_1$ is H, $R_2$ is selected from the group consisting of straight and branched alkyl groups containing 1–6 carbon atoms; and benzyl; and $R_3$ is selected from the group consisting of straight and branched alkyl groups containing 1–8 carbon atoms; phenyl; and benzyl;

23. $R_1$ is H, $R_2$ and $R_3$ are selected from the group consisting of straight and branched alkyl groups containing 1–4 carbon atoms; and benzyl;

24. $R_1$ is H, $R_2$ is selected from the group consisting of straight and branched alkyl groups containing 1–6 carbon atoms; and $R_3$ is selected from the group consisting of straight and branched alkyl groups containing 1–8 carbon atoms;

25. $R_1$ is H, and $R_2$ and $R_3$ are selected from the group consisting of straight and branched alkyl groups containing 1–4 carbon atoms;

26. $R_1$ is H, and $R_2$ and $R_3$ are benzyl (novel compound);

27. $R_1$ is H, $R_2$ is monosubstituted or disubstituted phenyl groups within the formula

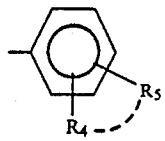

wherein $R_4$ and $R_5$ have the meanings given above and $R_3$ is selected from the group consisting of straight and branched alkyl groups containing 1–8 carbon atoms; and benzyl (novel compounds);

28. $R_1$ is H, $R_2$ is selected from the group consisting of straight and branched alkyl groups containing 1–6 carbon atoms; benzyl; unsubstituted, monosubstituted and disubstituted phenyl groups within the above formula

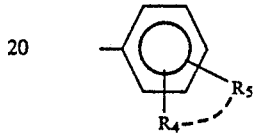

wherein $R_4$ and $R_5$ have the meanings given above; 1-adamantyl; and 2-adamantyl; and $R_3$ is selected from the group consisting of 1-adamantyl and 2-adamantyl (novel compounds);

29. $R_1$ is H, $R_2$ is 1-adamantyl or 2-adamantyl, and $R_3$ is selected from the group consisting of straight and branched alkyl groups containing 1–6 carbon atoms; benzyl; unsubstituted, monosubstituted and disubstituted phenyl groups within the above formula

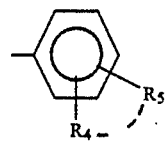

wherein $R_4$ and $R_5$ have the meanings given above; 1-adamantyl and 2-adamantyl (novel compounds);

30. $R_1$ is H, $R_2$ is selected from the group consisting of straight and branched alkyl groups containing 1–6 carbon atoms and benzyl; and $R_3$ is selected from the group consisting of monosubstituted or disubstituted phenyl groups within the formula

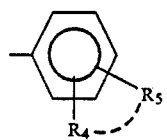

where $R_4$ and $R_5$ have the meanings given above;

31. $R_1$ and $R_3$ are H and $R_2$ is selected from the group consisting of straight and branched alkyl groups containing 1–6 carbon atoms; and benzyl;

32. $R_1$ and $R_3$ are H and $R_2$ is selected from the group consisting of straight and branched alkyl groups containing 1–4 carbon atoms and benzyl;

33. $R_1$ and $R_3$ are H and $R_2$ is selected from the group consisting of straight and branched alkyl groups containing 1–6 carbon atoms;

34. $R_1$ and $R_3$ are H and $R_2$ is selected from the group consisting of straight and branched alkyl groups containing 1-4 carbon atoms, that is methyl, ethyl, n-propyl, i-propyl, n-butyl, i-butyl, sec-butyl and t-butyl;

35. $R_1$ and $R_3$ are H and $R_2$ is benzyl;

36. $R_1$ and $R_3$ are H and $R_2$ is 1-adamantyl (novel compound);

37. $R_1$ and $R_3$ are H and $R_2$ is 2-adamantyl (novel compound);

38. Compounds of the formula I wherein $R_1$ and $R_2$ are hydrogen.

39. Compounds of the formula I wherein $R_1$ is hydrogen.

40. Compounds of the formula I wherein $R_1$ and $R_3$ are hydrogen.

Examples of compounds of the invention are given in the following table. In the right margin it is indicated whether the compound has been specifically disclosed in the prior art. All the other compounds are believed to be novel, and thus constitute a further aspect of the invention.

| $R_1$ | $R_2$ | $R_3$ | |
|---|---|---|---|
| H | H | $CH_3$ | prior art |
| H | H | $C_2H_5$ | prior art |
| H | H | $n-C_3H_7$ | |
| H | H | $i-C_3H_7$ | |
| H | H | $n-C_4H_9$ | |
| H | H | $sec.-C_4H_9$ | |
| H | H | $i-C_4H_9$ | prior art |
| H | H | $tert.-C_4H_9$ | |
| H | H | $n-C_5H_{11}$ | prior art |
| H | H | $n-C_6H_{13}$ | prior art |
| H | H | $n-C_7H_{15}$ | |
| H | H | $n-C_8H_{17}$ | |
| H | H | benzyl | prior art |
| H | H | 1-adamantyl | |
| H | H | 2-adamantyl | |
| H | $CH_3$ | $CH_3$ | prior art for $R_1 = Na$ |
| H | $CH_3$ | $C_2H_5$ | |
| H | $CH_3$ | $n-C_3H_7$ | |
| H | $CH_3$ | $i-C_3H_7$ | prior art for $R_1 = Na$ |
| H | $CH_3$ | $n-C_4H_9$ | prior art for $R_1 = \frac{1}{2} Ba^{2+}$ |
| H | $CH_3$ | $n-C_5H_{11}$ | |
| H | $CH_3$ | $n-C_6H_{13}$ | prior art for $R_1 = Na$ |
| H | $CH_3$ | $n-C_7H_{15}$ | |
| H | $CH_3$ | $n-C_8H_{17}$ | |
| H | $CH_3$ | phenyl | |
| H | $CH_3$ | benzyl | prior art |
| H | $C_2H_5$ | $CH_3$ | prior art for $R_1 = Na$ |
| H | $C_2H_5$ | $C_2H_5$ | |
| H | $C_2H_5$ | $n-C_3H_7$ | |
| H | $C_2H_5$ | $i-C_3H_7$ | |
| H | $C_2H_5$ | $n-C_4H_9$ | |
| H | $C_2H_5$ | $sec-C_4H_9$ | |
| H | $C_2H_5$ | $i-C_4H_9$ | |
| H | $C_2H_5$ | $tert-C_4H_9$ | |
| H | $C_2H_5$ | $n-C_5H_{11}$ | |
| H | $C_2H_5$ | $n-C_6H_{13}$ | |
| H | $C_2H_5$ | $n-C_7H_{15}$ | |
| H | $C_2H_5$ | $n-C_8H_{17}$ | |
| H | $C_2H_5$ | phenyl | |
| H | $C_2H_5$ | benzyl | prior art for $R_1 = Na$ |
| H | $n-C_3H_7$ | $CH_3$ | |
| H | $n-C_3H_7$ | $C_2H_5$ | prior art for $R_1 = Na$ |
| H | $n-C_3H_7$ | $n-C_3H_7$ | |
| H | $n-C_3H_7$ | $i-C_3H_7$ | |
| H | $n-C_3H_7$ | $n-C_4H_9$ | |
| H | $n-C_3H_7$ | $n-C_5H_{11}$ | |
| H | $n-C_3H_7$ | $n-C_6H_{13}$ | |
| H | $i-C_3H_7$ | $C_2H_5$ | |
| H | $n-C_4H_9$ | $CH_3$ | |
| H | $n-C_4H_9$ | $C_2H_5$ | prior art |
| H | $n-C_4H_9$ | $n-C_3H_7$ | |
| H | $n-C_4H_9$ | $i-C_3H_7$ | |
| H | $n-C_4H_9$ | $n-C_4H_9$ | |
| H | $n-C_4H_9$ | $n-C_5H_{11}$ | |
| H | $n-C_4H_9$ | phenyl | |
| H | $n-C_4H_9$ | benzyl | |
| H | $n-C_5H_{11}$ | $CH_3$ | |
| H | $n-C_5H_{11}$ | $C_2H_5$ | |
| H | $n-C_5H_{11}$ | $n-C_3H_7$ | |
| H | $n-C_5H_{11}$ | phenyl | |
| H | $n-C_6H_{13}$ | $CH_3$ | |
| H | $n-C_6H_{13}$ | $C_2H_5$ | |
| H | $n-C_7H_{15}$ | $CH_3$ | |
| H | $n-C_7H_{15}$ | $C_2H_5$ | |
| H | $n-C_8H_{17}$ | $CH_3$ | |
| H | $n-C_8H_{17}$ | $C_2H_5$ | |
| H | phenyl | $CH_3$ | |
| H | phenyl | $C_2H_5$ | |

-continued

| $R_1$ | $R_2$ | $R_3$ | |
|---|---|---|---|
| H | benzyl | $CH_3$ | |
| H | benzyl | $C_2H_5$ | prior art for $R_1$ = Na |
| H | phenyl | 1-adamantyl | |
| H | phenyl | 2-adamantyl | |
| H | 4-chlorophenyl | 1-adamantanyl | |
| H | 4-chlorophenyl | 2-adamantanyl | |
| H | 4-chlorophenyl | 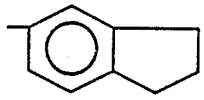 | |
| H | 4-methoxyphenyl | 1-adamantyl | |
| H | 4-methoxyphenyl | 2-adamantyl | |
| H | 4-methoxyphenyl | 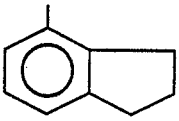 | |
| H | 4-methylphenyl | 1-adamantyl | |
| H | 4-methylphenyl | 2-adamantyl | |
| H | 1-adamantyl | 2-chlorophenyl | |
| H | 1-adamantyl | 2,3-chlorophenyl | |
| H | 1-adamantyl | 2,4-chlorophenyl | |
| H | 1-adamantyl | 4-chlorophenyl | |
| H | 1-adamantyl | 4-methoxyphenyl | |
| H | 1-adamantyl | 4-methylphenyl | |
| H | 1-adamantyl | 4-ethoxycarbonylphenyl | |
| H | 1-adamantyl | 1-adamantyl | |
| H | 2-adamantyl | 4-chlorophenyl | |
| H | 2-adamantyl | 3,4-dichlorophenyl | |
| H | 2-adamantyl | 4-methoxyphenyl | |
| H | 2-adamantyl | 4-methylphenyl | |
| H | 2-adamantyl | 4-ethoxycarbonylphenyl | |
| H | 2-adamantyl | 2-adamantyl | |
| $CH_3$ | $CH_3$ | $CH_3$ | prior art |
| $CH_3$ | $CH_3$ | $C_2H_5$ | prior art |
| $CH_3$ | $CH_3$ | n-$C_3H_7$ | |
| $CH_3$ | $CH_3$ | i-$C_3H_7$ | |
| $CH_3$ | $CH_3$ | n-$C_4H_9$ | |
| $CH_3$ | $CH_3$ | n-$C_5H_{11}$ | |
| $CH_3$ | $CH_3$ | n-$C_6H_{13}$ | |
| $CH_3$ | $CH_3$ | n-$C_7H_{15}$ | |
| $CH_3$ | $CH_3$ | n-$C_8H_{17}$ | |
| $CH_3$ | $CH_3$ | phenyl | |
| $CH_3$ | $CH_3$ | benzyl | prior art |
| $C_2H_5$ | $C_2H_5$ | $CH_3$ | prior art |
| $C_2H_5$ | $C_2H_5$ | $C_2H_5$ | prior art |
| $C_2H_5$ | $C_2H_5$ | n-$C_3H_7$ | |
| $C_2H_5$ | $C_2H_5$ | i-$C_3H_7$ | |
| $C_2H_5$ | $C_2H_5$ | n-$C_4H_9$ | |
| $C_2H_5$ | 4-methoxyphenyl | $C_2H_5$ | |
| $C_2H_5$ | $C_2H_5$ | sec-$C_4H_9$ | |
| $C_2H_5$ | $C_2H_5$ | i-$C_4H_9$ | |
| $C_2H_5$ | $C_2H_5$ | tert.-$C_4H_9$ | |
| $C_2H_5$ | $C_2H_5$ | n-$C_5H_{11}$ | |
| $C_2H_5$ | $C_2H_5$ | n-$C_6H_{13}$ | |
| $C_2H_5$ | $C_2H_5$ | n-$C_7H_{15}$ | |
| $C_2H_5$ | $C_2H_5$ | n-$C_8H_{17}$ | |
| $C_2H_5$ | $C_2H_5$ | phenyl | |
| $C_2H_5$ | $C_2H_5$ | benzyl | |
| n-$C_3H_7$ | n-$C_3H_7$ | $CH_3$ | |
| n-$C_3H_7$ | n-$C_3H_7$ | $C_2H_5$ | prior art |
| n-$C_3H_7$ | n-$C_3H_7$ | n-$C_3H_7$ | |
| n-$C_3H_7$ | n-$C_3H_7$ | i-$C_3H_7$ | |
| n-$C_3H_7$ | n-$C_3H_7$ | n-$C_4H_9$ | |
| n-$C_3H_7$ | n-$C_3H_7$ | n-$C_5H_{11}$ | |
| n-$C_3H_7$ | n-$C_3H_7$ | n-$C_6H_{13}$ | |
| i-$C_3H_7$ | i-$C_3H_7$ | $C_2H_5$ | prior art |
| n-$C_4H_9$ | n-$C_4H_9$ | $CH_3$ | |
| n-$C_4H_9$ | n-$C_4H_9$ | $C_2H_5$ | prior art |
| n-$C_4H_9$ | n-$C_4H_9$ | n-$C_3H_7$ | |
| n-$C_4H_9$ | n-$C_4H_9$ | i-$C_3H_7$ | |
| n-$C_4H_9$ | n-$C_4H_9$ | n-$C_4H_9$ | |
| n-$C_4H_9$ | n-$C_4H_9$ | n-$C_5H_{11}$ | |
| n-$C_4H_9$ | n-$C_4H_9$ | phenyl | prior art |

-continued

| $R_1$ | $R_2$ | $R_3$ | |
|---|---|---|---|
| n-$C_4H_9$ | n-$C_4H_9$ | benzyl | |
| n-$C_5H_{11}$ | n-$C_5H_{11}$ | $CH_3$ | |
| n-$C_5H_{11}$ | n-$C_5H_{11}$ | $C_2H_5$ | |
| n-$C_5H_{11}$ | n-$C_5H_{11}$ | n-$C_3H_7$ | |
| n-$C_5H_{11}$ | n-$C_5H_{11}$ | phenyl | |
| n-$C_6H_{13}$ | n-$C_6H_{13}$ | $CH_3$ | |
| n-$C_6H_{13}$ | n-$C_6H_{13}$ | $C_2H_5$ | |
| n-$C_7H_{15}$ | n-$C_7H_{15}$ | $CH_3$ | |
| n-$C_7H_{15}$ | n-$C_7H_{15}$ | $C_2H_5$ | |
| n-$C_8H_{17}$ | n-$C_8H_{17}$ | $CH_3$ | |
| n-$C_8H_{17}$ | n-$C_8H_{17}$ | $C_2H_5$ | |
| phenyl | phenyl | $CH_3$ | |
| phenyl | phenyl | $C_2H_5$ | prior art |
| phenyl | phenyl | phenyl | |
| benzyl | benzyl | $CH_3$ | |
| benzyl | benzyl | $C_2H_5$ | |
| 4-methylphenyl | 4-methylphenyl | ethyl | |
| 4-methoxyphenyl | ethyl | phenyl | |
| 4-chlorophenyl | ethyl | phenyl | |
| 3,4-dichlorophenyl | ethyl | phenyl | |
| methyl | methyl | 4-methylphenyl | |
| methyl | methyl | 3,4-dichlorophenyl | |
| methyl | methyl | 2-adamantyl | |
| ethyl | ethyl | 4-methoxyphenyl | |
| ethyl | ethyl | 4-chlorophenyl | |
| ethyl | ethyl | 4-ethoxycarbonylphenyl | |
| ethyl | ethyl | 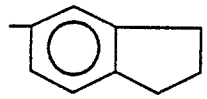 | |
| 2,3-dichlorophenyl | phenyl | ethyl | |
| methyl | methyl | 2,6-dimethylphenyl | |
| 2-methyl-4-chlorophenyl | ethyl | phenyl | |
| 2-adamantyl | methyl | ethyl | |
| 1-adamantyl | methyl | methyl | |
| H | $CH_3$ | H | (prior art) |
| H | $C_2H_5$ | H | (prior art) |
| H | n-$C_3H_7$ | H | |
| H | i-$C_3H_7$ | H | |
| H | n-$C_4H_9$ | H | (prior art) |
| H | iso-$C_4H_9$ | H | |
| H | sec-$C_4H_9$ | H | |
| H | tert-$C_4H_9$ | H | |
| H | n-$C_5H_{11}$ | H | |
| H | n-$C_6H_{13}$ | H | |
| H | benzyl | H | (prior art) |
| H | 1-adamantyl | H | |
| H | 2-adamantyl | H | |

Particularly preferred compounds are:

| $R_1$ | $R_2$ | $R_3$ | Code |
|---|---|---|---|
| H | H | $C_2H_5$ | VIS 210 |
| H | H | n-$C_4H_9$ | VIS 418 |
| H | H | benzyl | VIS 409 |
| H | H | i-$C_3H_7$ | VIS 420 |
| H | H | 2-adamantyl | VIS 131 |
| H | $C_2H_5$ | $C_2H_5$ | VIS 414 |
| H | n-$C_4H_9$ | $CH_3$ | VIS 047 |
| H | $CH_3$ | benzyl | VIS 406 |
| H | phenyl | $C_2H_5$ | VIS 036 |
| $C_2H_5$ | $C_2H_5$ | $C_2H_5$ | EHB 783 (prior art) |
| $C_2H_5$ | $C_2H_5$ | $CH_3$ | VIS 224 (prior art) |
| n-$C_4H_9$ | n-$C_4H_9$ | $CH_3$ | VIS 046 |
| $CH_3$ | $CH_3$ | n-$C_4H_9$ | VIS 415 |
| $CH_3$ | $CH_3$ | phenyl | VIS 416 |
| $CH_3$ | $CH_3$ | benzyl | VIS 405 |
| phenyl | phenyl | $C_2H_5$ | VIS 035 (prior art) |
| benzyl | benzyl | $C_2H_5$ | VIS 201 |
| $CH_3$ | $CH_3$ | i-$C_3H_7$ | VIS 419 |
| 4-methoxyphenyl | ethyl | phenyl | VIS 057 |

-continued

| $R_1$ | $R_2$ | $R_3$ | Code |
|---|---|---|---|
| 4-chlorophenyl | ethyl | phenyl | VIS 061 |
| 3,4-dichlorophenyl | ethyl | phenyl | VIS 062 |
| methyl | methyl | 4-methylphenyl | VIS 128 |
| methyl | methyl | 3,4-dichlorophenyl | VIS 134 |
| methyl | methyl | 2-adamantyl | VIS 129 |
| ethyl | ethyl | 4-methoxyphenyl | VIS 236 |
| ethyl | ethyl | 4-chlorophenyl | VIS 237 |
| $CH_3$ | $CH_3$ | cyclo-$C_6H_{11}$ | VIS 137 |
| $CH_3$ | $CH_3$ | $CH_2$—cyclo-$C_5H_9$ | VIS 140 |
| $CH_3$ | 1-adamantyl | $CH_3$ | VIS 077 |
| $C_2H_5$ | $C_2H_5$ | 4-ethoxycarbonylphenyl | VIS 241 |
| $CH_3$ | $CH_3$ | 4-ethoxycarbonylphenyl | VIS 243 |
| $C_2H_5$ | 2,6-dimethylphenyl | $CH_3$ | VIS 435 |
| $C_2H_5$ | 5-indanyl | $CH_3$ | VIS 436 |
| $CH_3$ | 4-acetylphenyl | $CH_3$ | VIS 072 |
| H | H | Cyclo-$C_6H_{11}$ | VIS 138 |
| H | H | $CH_2$—cyclo-$C_6H_{11}$ | VIS 141 |
| H | 1-adamantyl | $CH_3$ | VIS 079 |

-continued

| R₁ | R₂ | R₃ | Code |
|---|---|---|---|
| H | 5-indanyl | CH₃ | VIS 441 |
| H | 2,6-dimethyl-phenyl | CH₃ | VIS 439 |
| H | 1-adamantyl | H | VIS 078 |
| H | CH₃ | H | VIS 018 (prior art) | and physiologically acceptable salts thereof.

Salts of the active substances

Physiologically acceptable salts of those active substances of the formula I which form salts are prepared by methods known in the art as illustrated in the following.

Examples of metal salts which can be prepared are salts containing Li, Na, K, Ca, Mg, Zn, Mn and Ba. A less soluble metal salt can be precipitated from a solution of a more soluble salt by addition of a suitable metal compound. Thus for examples, Ca, Ba, Zn, Mg, and Mn salts of the active substances can be prepared from sodium salts thereof. The metal ion of a metal salt of the active substances can be exchanged by hydrogen ions, other metal ions, ammonium ion and ammonium ions substituted by one or more organic radicals by using a cation exchanger.

Examples of other useful salts which can be prepared in this way are the salts of the formula

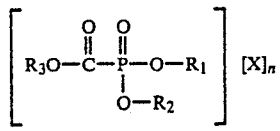

III in which formula $R_1$ $R_2$ and $R_3$ have the same meaning as above, n is 1 or 2, and X is a salt-forming component such as NH₃, CH₃NH₂, C₂H₅NH₂, C₃H₇NH₂, C₄H₉NH₂, C₅H₁₁NH₂, C₆H₁₃NH₂, (CH₃)₂NH, (C₂H₅)₂NH, (C₃H₇)₂NH, (C₄H₉)₂NH, (C₅H₁₁)₂NH, (C₆H₁₃)₂NH, (CH₃)₃N, (C₂H₅)₃N, (C₃H₇)₃N, (C₄H₉)₃N, (C₅H₁₁)₃N, (C₆H₁₃)₃N, C₆H₅CH₂NH₂, HOCH₂CH₂NH₂, (HOCH₂CH₂)₂NH, (HOCH₂CH₂)₃N, C₂H₅NH(CH₂CH₂OH), C₂H₅N(CH₂CH₂OH)₂, (HOH₂C)₃CNH₂ and

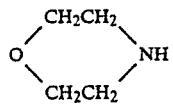

Further examples of other useful salts which can be prepared by the ion exchange technique are quaternary ammonium salts of the active substances, i.e. salts in which the hydrogens in the active substances (structural formula I) have been substituted with quarternary ammonium ions such as (CH₃)₄N, (C₃H₇)₄N, (C₄H₉)₄N, (C₅H₁₁)₄N, (C₆H₁₃)₄N and C₂H₅N(CH₂CH₂OH)₃. Lipophilic salts of this type can also be prepared by mixing a salt of the active substances with a quaternary ammonium salt in water and extracting out the resulting quaternary ammonium salt of the active substances with an organic solvent such as dichloromethane, chloroform, ethyl acetate and methyl isobutyl ketone.

The compounds utilized within the invention may be formulated for use in human and veterinary medicine for therapeutic and prophylactic use. The compounds may be used in the form of a physiologically acceptable salt. Suitable salts are e.g. amine salts, e.g. dimethylamine and triethylamine salt, ammonium salt tetrabutylammonium salt, cyclohexylamine salt, dicyclohexylamine salt; and metal salts, e.g. mono-, and disodium salt, mono- and dipotassium salt, magnesium salt, calcium salt and zinc salt.

The compounds utilized within the invention are particularly useful for systemic treatment of virus infections, by oral administration or by injection. In comparison with phosphonoformic acid, they are generally more stable in acid solutions, and are thus less readily decomposed in the stomach.

In comparison with phosphonoformic acid the compounds of the present invention are more lipophilic and are thus more suitable to treat virus infections in organs for which penetration through lipid barriers are of importance.

In clinical practice the compound will normally be administered topically, orally, intranasally, by injection or by inhalation in the form of a pharmaceutical preparation comprising the active ingredient in the form of the original compound or optionally in the form of pharmaceutically acceptable salt thereof, in association with a pharmaceutically accaptable carrier which may be a solid, semi-solid or liquid diluent or an ingestible capsule, and such preparations comprise a further aspect of the invention. The compound may also be used without carrier material. As examples of pharmaceutical preparations may be mentioned tablets, drops such as nasal and eye drops, preparations for topical application such as ointments, jellies, creams and suspensions, aerosols for inhalation, nasal spray, liposomes, etc. Usually the active substance will comprise between 0.05 and 99, or between 0.1 and 99% by weight of the preparation, for example between 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragées. If dragées are required, the cores may be coated for example with concentrated sugar solutions which may contain gum arabic, talc and/or titainium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax ® or a suitable oil as e.g. sesam oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of oral preparations—tablets, capsules, etc.—which are designed so as to prevent release of and possible decomposition of the active substance in the gastric juice, the tablets, dragées etc. may be enteric coated, that is provided with a layer of a gastric juice resistant enteric film or coating having such properties that it is not dissolved at the acidic pH in the gastric juice. Thus, the active substance will not be released until the preparation reaches the intestines. As examples of such known enteric coatings may be mentioned cellulose acetate phtalate, hydroxypropylmethylcellulose phtalates such as those sold under the trade names HP 55 and HP 50, and Eudragit®L and Eudragit®S.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture or ethanol, water, glycerol, propylene glycol and optionally aroma, saccharine and/or carboxymethylcellulose as a dispersing agent.

For parenteral application by injection preparations may comprise an aqueous suspension of the active compounds according to the invention, desirably in a concentration of 0.5–10%, and optionally also a stabilizing agent and/or buffer substances in aqueous solution. Dosage units of the solution may advantageously be enclosed in ampoules.

For topical application, especially for the treatment of herpes virus infections on skin, genitals and in mouth and eyes the preparations are suitably in the form of a solution, ointment, gel, suspension, cream or the like. The amount of active substance may vary, for example between 0.05–20% by weight of the preparation. Such preparations for topical application may be prepared in known manner by mixing the active substance with known carrier materials such as isopropanol, glycerol, paraffine, stearyl alcohol, polyethylene glycol, etc. The pharmaceutically acceptable carrier may also include a known chemical absorption promotor. Examples of absorption promoters are e.g. dimethylacetamide (U.S. Pat. No. 3,472,931), trichloroethanol or trifluoromethanol (U.S. Pat. No. 3,891,757), certain alcohols and mixtures thereof (British Pat. No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the active ingredients are administered may vary within a wide range and will depend on various factors such as for example the severity of the infection, the age of the patient, etc., and may have to be individually adjusted. As a possible range for the amount of the active substance which may be administered per day may be mentioned from about 0.1 mg to about 2000 mg or from about 1 mg to about 2000 mg, or preferably from 1 mg to about 2000 mg for topical administration, from 50 mg to about 2000 mg or from 100 to 1000 mg for oral administration and from 10 mg to about 2000 mg or from 50 to 500 mg for injection. In severe cases it may be necessary to increase these doses 5-fold to 10-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that the above compounds, and the physiologically acceptable salts thereof can be used to selectively inhibit the multiplication of viruses and the compounds and physiologically acceptable salts thereof are therefore useful in therapeutic and/or propylactic treatment of virus infections as described above.

Preparation of the active substances

Reference to "meaning given above" for $R_1$, $R_2$ and $R_3$ as used below refers to the definitions given in formula I.

The hydroxycarbonylphosphoric acid triesters may be prepared by known methods for example as described in Houben-Weyl, Methoden der Organischen Chemie, Auflage 4, Band XII, Teil 1, Organische Phosphorverbiindungen, p. 433–463. Examples of such methods are the following.

A. Reacting formic acid ester compounds with phosphite triesters according to the formula:

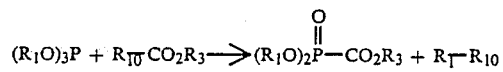

wherein $R_1$ and $R_3$ have the meaning given above except that $R_1$ must not be phenyl or substituted phenyl. $R_{10}$ is a leaving group suitable for Arbuzov type reactions, such as Cl, Br, I, sulphonate, carboxylate, alkoxide.

Preferably the reaction is performed at 0° to 150° for 1 to 50 hours.

B. Reacting formic acid ester compounds with phosphite triesters according to the formula:

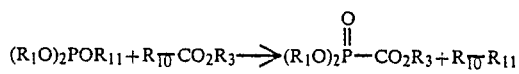

wherein $R_1$, $R_3$ and $R_{10}$ have the meaning given above. $R_{11}$ may be an alkyl, a cycloalkyl, a cycloalkyl-alkyl, a benzyl, an adamantyl or any phosphite esterifying group suitable for participation in Arbuzov type reactions.

Preferably the reaction is performed at 0° to 150° for 1 to 50 hours.

C. Reacting formic acid ester compounds with phosphite triesters according to the formula:

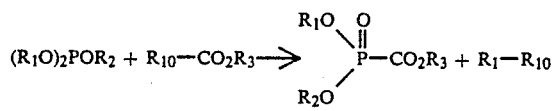

wherein $R_1$, $R_2$, $R_3$ and $R_{10}$ have the meaning given above, except that $R_1$ must not be phenyl or a substituted phenyl.

D. Reacting formic acid ester compounds with phosphite diester salts according to the formula:

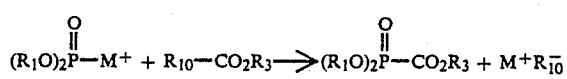

wherein $R_1$, $R_3$ and $R_{10}$ have the meaning given above and $M^+$ is a cation, preferably a metal such as $Li^+$, $Na^+$ or $K^+$, and the reaction is preferably performed at 0° to 100° for 1 to 50 hours in a solvent such as for example, toluene, ether or tetrahydrofurane.

The phosphite diester salts are prepared by treating the phosphite diester with a suitable proton abstracting compound, such as a metal alkoxide, suitably free from alcohol, such as litium-, sodium- or potassium methoxide, ethoxide or t-butoxide, or with a hydride such as sodium- or potassium hydride, or with a base such as butyllithium.

The starting materials used in the above methods of preparation A-D are known compounds, or may be prepared by known methods commonly used for the synthesis of formate esters and phosphite triesters. Examples of methods used for the synthesis of haloformate esters may be found in, or referred to in M. Matzner et al Chem. Rev. 64 (1964) 645. Examples of methods used for the synthesis of phosphite triesters may be found in Houben-Weyl, Methoden der Organischen Chemie, Auflage 4, Band XII, Teil 2, Organische Phosphorverbindungen, p. 5–78.

E. Esterification of the phosphoric acid groups of hydroxycarbonylphosphonic acid monoester according to the formula:

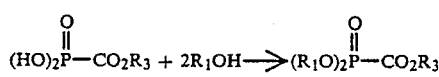

$R_1$ and $R_3$ have the meaning given above. The reaction is performed through the intermediary of activating agents known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297.

Synthesis of monoesters of the carboxylic group of hydroxycarbonylphosphonic acid are described below in methods T–X.

F. Esterification of hydroxycarbonylphosphonic acid diesters according to the formula:

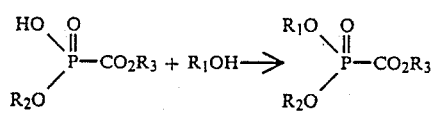

$R_1$, $R_2$ and $R_3$ have the meaning given above.

The reaction is performed through the intermediary of activating agents known per se for the phosphorylation of alcohols and phenols. Examples of such methods are described for example by L. A. Slotin in Synthesis 1977, 737, and by H. Seliger and K. Kössel in Progress in the Chemistry of Organic Natural Products 32 (1975) 297.

Synthesis of hydroxycarbonylphosphonic acid diesters are described below in methods K–O.

G. Reacting oxycarbonylphosphonic acid dihalide esters according to the formula:

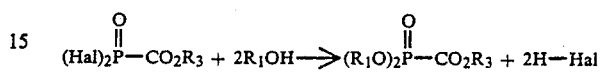

Hal is Cl, Br or I and $R_1$ and $R_3$ have the meaning given above.

The reaction is performed by methods known per se for the phosphorylation of alcohols and phenols by phosphoric and phosphonic acid halides. Examples of such methods are described for example by L. A. Slotin in Synthesis 1977, 737 and by H. Seliger and H. Kössel in Progress in the Chemistry of Organic Natural Products 32 (1975) 297.

The oxycarbonylphosphonic acid dihalide esters are prepared from oxycarbonylphosphonic acid monocarboxylic esters by methods known per se for the synthesis of dihalides of phosphoric acids and phosphonic acids. References for these methods are found for example in the two publications above and in Houben-Weyl, Methoden der Organischen Chemie, Auflage 4, Band XII/1, p. 386–406 and Band XII/2 p. 211–225 and p. 274–292.

Oxycarbonylphosphonic acid monocarboxylic esters are prepared by methods described below in T–X.

H. Reacting oxycarbonylphosphonic acid monohalide diesters according to the formula:

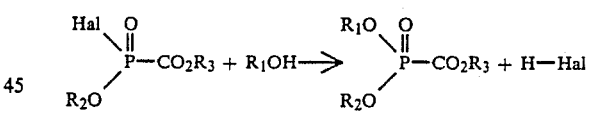

Hal is Cl, Br or I and $R_1$, $R_2$ and $R_3$ have the meaning given above.

The reaction is performed by methods known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297.

Oxycarbonylphosphonic acid monohalide diesters are prepared from oxycarbonylphosphonic acid diesters by methods known per se for the synthesis of monohalides of phosphonic and phosphoric acids. References for those methods are found for example in the two publications above and in Houben-Weyl, Methoden der Organischen Chemie, Auflage 4, Band XII/1 p. 386–406 and XII/2 p. 211–225 and p. 274–292.

Oxycarbonylphosponic acid diesters are prepared by methods described below in K–O.

J. Reacting a carbonylphosphonic acid diester according to the formula

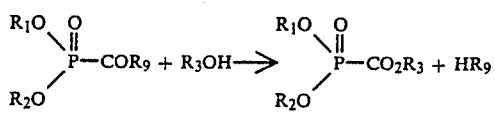

$R_1$, $R_2$ and $R_3$ have the meaning given above and $R_9$ is a suitable activating moiety, known per se as a good leaving group in substitution reactions on activated carboxylic acid groups. Preferably $R_9$ is a group such as for example p-nitrophenoxy or imidazolyl.

The activated carbonylphosphonic acid diester used as a starting material may for example be prepared by methods analogous to these described above in A–D.

Diesters of hydroxycarbonylphosphonic acid are prepared by known methods, such as K. Reacting a hydroxycarbonylphosphonic acid triester with an iodide or a bromide anion, according to the formula:

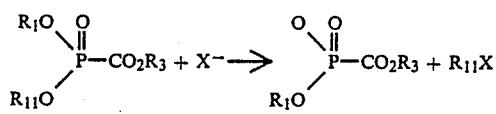

wherein X is Br or I and $R_1$, $R_3$ and $R_{11}$ have the meaning given above.

Preferably the reaction is carried out with sodium iodide in a solvent such as for example tetrahydrofuran or acetone. Preferably the reaction is carried out at a temperature from 20° to 100° from 2 hours to 7 days.

The hydroxycarbonylphosphonic acid triesters may be prepared by methods analogous to these described above in A–H.

I. Hydrolysing the hydroxycarbonylphosphonic acid triester with a base according to the formula:

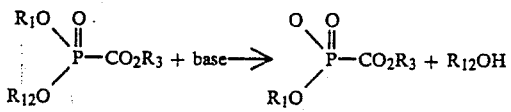

$R_1$, and $R_3$ have the meaning given above. $R_{12}$ is a hydrolyzable phosphate ester group. For example it may have the meaning given $R_1$ and $R_2$ and it may for example be a more generally substituted aryl group.

Preferably the reaction is carried out with a base such as for example sodium hydrogencarbonate, sodiumcarbonate or sodium hydroxide in water at a temperature from 20° to 100° from 2 hours to 7 days. The hydroxycarbamylphosphonic acid triesters may be prepared by methods analogous to those described above.

M. Aqueous hydrolysis of a hydroxycarbonylphosphonic acid triester, containing one silyl esterified phosphonate group according to the formula:

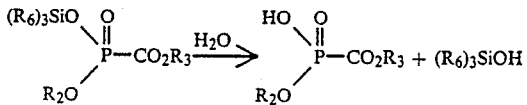

where $R_2$ and $R_3$ have the meaning given above and $R_6$ is an inert organic residue, preferably an organic group such as for example $CH_3$. Another example of silylester groups are for example butyldiphenylsilyl compounds, which have been described by R. A. Jones et al Bichemistry 17 (1978) 1268 as phosphate ester derivatives.

Optionally the formed phosphonic acid group may be neutralized. Preferably it may be neutralized with a base such as for example $MHCO_3$, $M_2CO_3$ or $MOH$ or with a weak cation exchanger ($M^+$), where $M^+$ is $NH_4^+$ or a metal such as $Li^+$, $Na^+$, or $K^+$.

The silyl esterified phosphonate group may be obtained by treating the hydroxycarbonylphosphonic acid triester with a halosilane according to the formula:

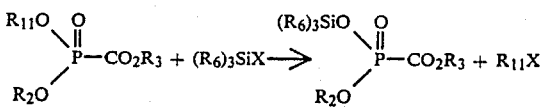

X is Cl, Br or I and $R_2$, $R_3$ $R_6$ and $R_{11}$ have the meaning given above.

Preferably the reagents used for silylation are for example bromotrimethylsilane at −20° to 50° for ½ to 20 hours, or alternatively for example chlorotrimethylsilane at 20° to reflux temperature for several days.

The hydroxycarbonylphosphonic acid triesters are prepared by methods analogous to those described above in A–J.

Alternatively the silyl esterified phosphonate group may be prepared by reacting a phosphite triester containing two silyl ester groups, with a formate ester, according to the formula:

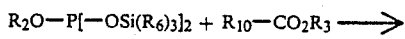

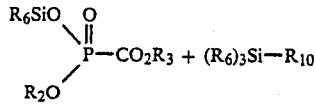

$R_2$, $R_3$, $R_6$ and $R_{10}$ have the meaning given above.

Preferably the phosphite is an ester such as for example a bis-(trimethylsilylated)phosphite triester. These compounds can be prepared by methods known per se. For example the synthesis of propyl- and cyclohexyl-bis(trimethylsilyl)phosphites are described in T. R. Herrin et al, J Med Chem 20 (1977) 660.

N. Reacting oxycarbonylphosphonic acid monocarboxylic esters according to the formula:

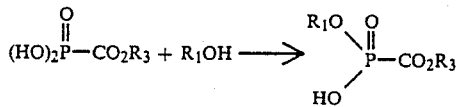

$R_1$ and $R_3$ have the meaning given above. The reaction is performed through the intermediary of activating agents known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297. Optionally the phosphonic acid group may be neutralized.

Synthesis of oxycarbonylphosphonic acid monocarboxylic acids are described below in methods T–X.

O. Reacting hydroxycarbonylphosphonic acid mono-P ester with an esterifying halide, using a tetraalkylammonium salt as a catalyst, according to the formula:

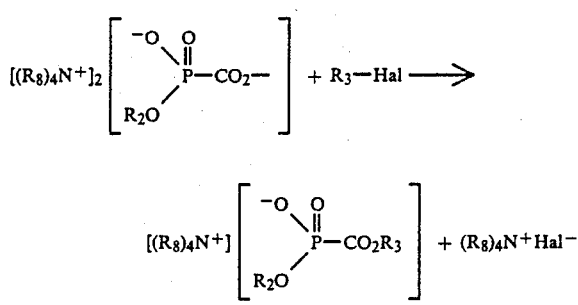

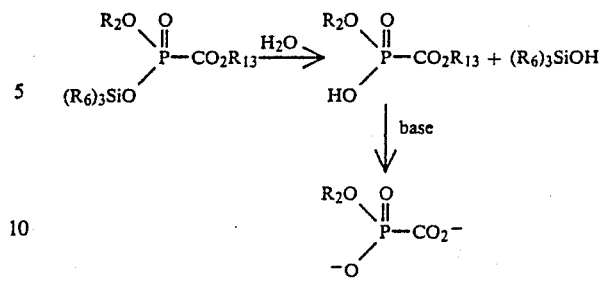

Hal is Cl, Br or I, $R_2$ and $R_3$ have the meaning given above and $R_8$ is an alkyl residue such as for example n-butyl, n-pentyl, n-hexyl, n-heptyl and n-octyl. Preferably n-heptyl is used and preferably the reaction is performed as an extractive alkylation as described by for example A. Brändström in Preparative Ion Pair Extraction (Apotekersooieteton, Hässle, Sweden 1976).

Also as described the phosphonate group may be transformed to a salt

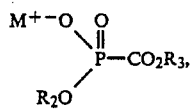

where $M^+$ is for example $NH_4^+$ or a metal such as $Li^+$, $Na^+$ or $K^+$.

The synthesis of hydroxycarbonylphosphonic acid mono-P esters are described below in methods P-S.

Monoesters of the phosphonic group of hydroxycarbonylphosphonic acid are prepared by known methods such as, P. Hydrolyzing a hydroxycarbonylphosphonic acid triester according to the formula:

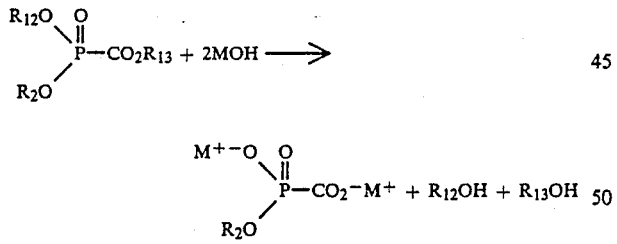

wherein M is a cation such as $NH_4^+$ or $Li^+$, $Na^+$ or $K^+$ and wherein $R_{12}$ has the meaning given above. $R_{13}$ has the meaning given $R_{12}$ and $R_{12}$ and $R_{13}$ may be the same or different. $R_2$ is defined above except that it must not be phenyl or substituted phenyl.

Preferably the reaction is carried out in water at 20° to 100° for 1 to 10 hours.

The hydroxycarbonylphosphonic acid triesters are prepared by methods analogous to those described above in A–J.

Q. By the stepwise deesterification of a phosphonic acid trisubstituted silyl ester group, and the carboxylic acid ester group, of hydroxycarbonylphosphonic acid triesters, according to the formula:

$R_6$ and $R_{13}$ have the meaning given above, and the silyl ester group is preferably a group such as exemplified above in method M. $R_2$ is as defined above except that it must not be phenyl or substituted phenyl.

The trimethylsilyl ester group is preferably hydrolyzed with water and the free acid group is preferably converted to a salt by a weak cation exchanger ($M^+$) or with an aqueous base such as $MHCO_3$, $M_2CO_3$ or MOH.

The carboxylic acid ester group is preferably hydrolyzed in water and neutralized with a weak cation exchanger ($M^+$) or with for example an aqueous base such as $MHCO_3$, $M_2CO_3$ or MOH.

$M^+$ is $NH_4^+$ or a metal such as Li, Na or K.

Compounds containing the silylesterified phosphonate group may be prepared by known methods as described in method M above.

R. By the stepwise deesterification of the silyl- and the benzyl ester group of alkyl, silyl benzyloxycarbonylphosphonate according to the formula:

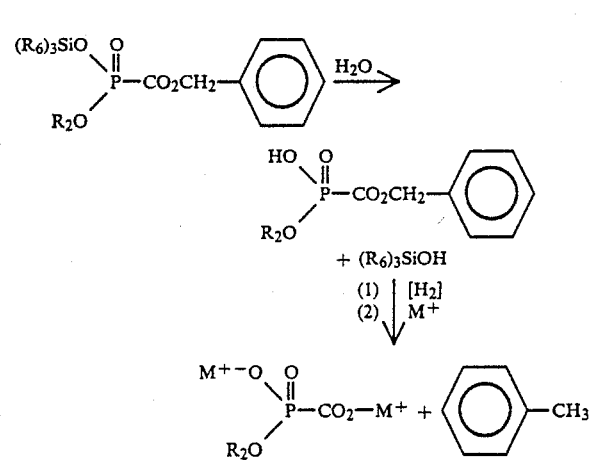

$M^+$ is $NH_4^+$ or a metal such as for example $Li^+$, $Na^+$ or $K^+$, and $R_2$ and $R_6$ have the meaning given above except that $R_2$ must not be benzyl, phenyl or substituted phenyl. The silyl ester group is preferably a group such as described above in method M.

The benzyl ester group is preferably hydrogenated with a catalyst such as for example palladiumcarbon. The free acid groups are converted to their metal salts by the treatment with a weak cation exchanger ($M^+$) or with a base such as for example $MHCO_3$, $M_2CO_3$ or MOH.

The silylated compound may be prepared by known methods, analogous to those described above in M.

S. By the deesterification of the bis-silylester groups (on the phosphonic and on the carboxylic acid groups)

of hydroxycarbonylphosphonic acid triesters according to the formula:

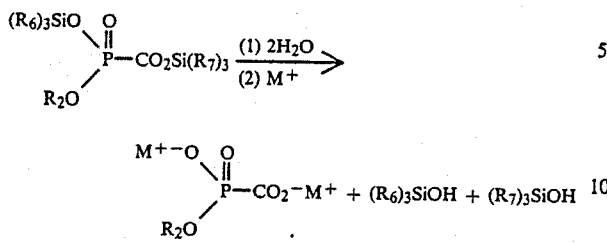

$R_2$ has the meaning given above. $R_6$ and $R_7$ are inert organic residues, the same or different, preferably they are the same and a group such as for example $CH_3$. The silyl ester groups may also be for example butyldiphenylsilyl groups as described above in method M. $M^+$ is $NH_4^+$ or a metal such as $Li^+$, $Na^+$ or $K^+$.

The silyl ester groups are preferably hydrolyzed with for example water and neutralized with for example a weak cation exchanger ($M^+$) or an aqueous base such as $MHCO_3$, $M_2CO_3$ or $MOH$.

The bis-silylated triester of hydroxycarbonylphosphonic acid may be prepared by methods known per se, according to the formula

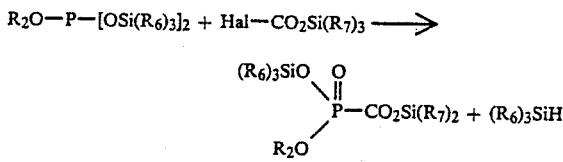

Hal is Cl, Br or I and $R_2$, $R_6$ and $R_7$ have the meaning given above.

Preferably the phosphite is an ester such as for example a bis(trimethylsilylated)phosphite triester. These compounds can be prepared as described above in M.

The haloformate silylesters may be prepared according to the formula:

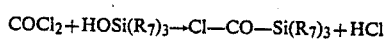

$R_7$ has the meaning given above.

The reaction is carried out under anhydrous conditions, and preferably a base such as for example N,N-dimethylaniline is used for capturing the released hydrogenchloride. The reaction is preferably carried out in an inert solvent such as for example toluene or ether, at for example $-10°$ to $25°$ for 1 to 25 hours.

Monoesters of the carboxylic group of hydroxycarbonylphosphonic acid are prepared by known methods, such as T. Aqueous hydrolysis of a hydroxycarbonylphosphonic acid triester, containing two silyl esterified phosphonate groups, according to the formula:

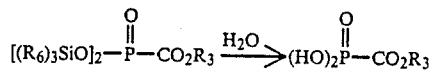

$R_3$ and $R_6$ have the meaning given above. Preferably $R_6$ is for example $CH_3$. The silyl ester derivatives may also be for example butyldiphenylsilyl groups as described above in method M.

Optionally the formed phosphonic acid groups can be neutralized. Preferably they may be neutralized with a weak cation exchanger ($M^+$) or with a base such as $MHCO_3$, $M_2CO_3$ or $MOH$. $M^+$ is $NH_4^+$ or a metal such as $Li^+$, $Na^+$ or $K^+$.

The phosphonate bis-silyl esters may be obtained according to the formula:

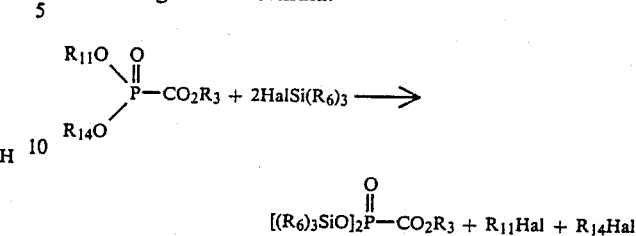

$R_3$, $R_6$ and $R_{11}$ have the meaning given above. $R_{14}$ has the meaning given $R_{11}$ and $R_{11}$ and $R_{14}$ may be the same or different. Preferably the organic residues of the silyl group are as described above. Hal is Cl, Br or I and preferably the reaction is performed at $-20°$ to reflux temperatures for 1 hour to several days.

The hydroxycarbonylphosphonic acid triesters are prepared by methods analogous to those described in A–J.

Alternatively the bis silylphosphonate esters may be prepared by reacting a trissilylphosphite with a halogenformate ester according to the formula:

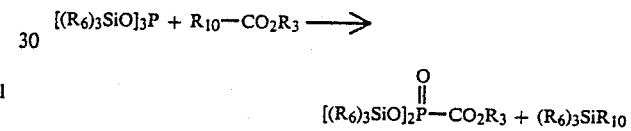

$R_3$, $R_6$ and $R_{10}$ have the meaning given above and preferentially the organic residues of silyl groups are as described above. Preferably the reaction is performed at $20°-150°$ for 1 to 25 hours.

The tris-silyl phosphosphites are prepared by known methods, as described for example by Herrin et al in J. Med. Chem. 20 (1977) 660, for the preparation of tris(-trimethylsilyl)phosphite.

U. Reacting triesters of hydroxycarbonylphosphonic acid with hydrogenhalide acids according to the formula:

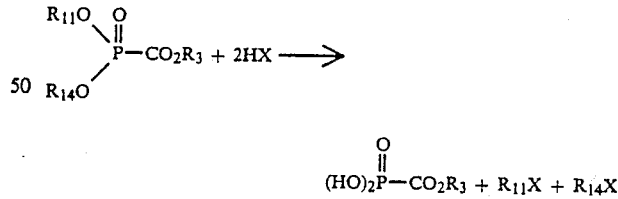

$R_3$, $R_{11}$ and $R_{14}$ have the meaning given above. X is Cl, Br or I.

Preferably HI may be used and the reaction may preferably be performed in a dry solvent such as methylene chloride or acetic acid at a temperature from $0°$ to $30°$. Examples of the reaction may be found in the patents U.S. Pat. No. 3,943,201 and OT-OLS 2435 407.

Optionally the phosphonic acid groups may be neutralized. Preferably a weak cation exchanger ($M^+$) or a base such as $MHCO_3$, $M_2CO_3$ or $MOH$ is used. $M^+$ is for example $NH_4^+$ or a metal such as $Li^+$, $Na^+$ or $K^+$.

V. Hydrogenating dibenzyl, alkyl-oxycarbonylphonates according to the formula:

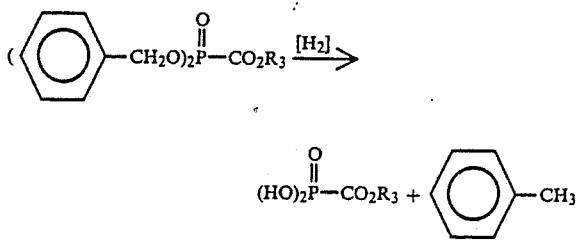

R₃ has the meaning given above, except that it should not be benzyl, phenyl or substituted phenyl.

Preferably the reaction may be performed with a catalyst such as palladiumcarbon. Optionally the phosphonic acid groups may be neutralized. Preferably they may be neutralized with a weak cation exchanger (M+) or with a base such as $MHCO_3$, $M_2CO_3$ or MOH. M+ is for example $NH_4^+$ or a metal such as $Li^+$, $Na^+$ or $K^+$.

W. Reacting hydroxycarbonylphosphonic acid with an esterifying halide, using a tetraalkylammonium salt as a catalyst, according to the formula:

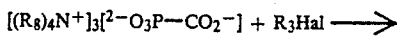

Hal is Cl, Br or I. R₃ has the meaning given above and R₈ an alkyl residue, such as for example n-butyl, n-pentyl, n-hexyl, n-heptyl and n-octyl. Preferably n-heptyl is used and preferably the reaction is performed as an extractive alkylation, as described by for example A Brändström, Preparative Ion Pair Extraction (Apotekarsocieteten, Hässle, Sweden 1976).

Also as described, the phosphonate groups may be transformed to a disalt

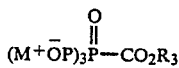

where M+ is for example $NH_4^+$ or a metal such as $Li^+$, $Na^+$ or $K^+$.

X. Reacting oxycarbonylphosphonic acid diesters according to the formula

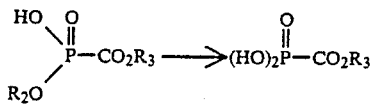

R₂ and R₃ have the meaning described above.

The preparations may be performed by procedures analogous to those described above in T–V.

Optionally the oxycarbonylphosphonic acid monocarboxylic ester thus obtained may be neutralized with a weak cation exchanger or with a base such as $MHCO_3$, $M_2CO_3$ or MOH. M+ is for example $NH_4^+$ or a metal such as $Li^+$, $Na^+$ or $K^+$.

The oxycarbonylphosphonic acid diesters may be prepared by methods described above in K–N.

Preparations of triesters of hydroxycarbonylphosphonic acid.

EXAMPLE 1

Diethyl 4-methoxyphenoxycarbonylphosphonate 18.6 g (0.12 mole) of triethylphosphite was heated at 125°–130° C. in a flask with a reflux condensor. 18.6 g (0.10 mole) of 4-methoxyphenyl chloroformate (prepared according to M. J. Zabik and R. D. Schuetz, J. Org. Chem. 32 (1967) 300) was added dropwise. The reaction flask was heated additionally at about 120° C. for 1,5 hours and left at room temperature overnight. The product was distilled to give 25.8 g (89%) of diethyl 4-methoxyphenoxycarbonylphosphonate. $Bp_{0.03}=174°–8°$ C., $n_D^{21}=1.4940$.

Analysis for $C_{12}H_{17}O_6P$. Found (calculated): C 49.79 (50.00), H 6.01 (5.95), P 10.54 (10.75).

NMR (CDCl₃) δ: 1.42 (t, CH₃), 3.78 (S, OCH₃), 4.13–4.63 (CH₂), 6.77–7.33 (aromatic).

IR (neat) $cm^{-1}$: 1740 (CO), 1275, 1255, 1190, 1030.

EXAMPLE 2

By mixing the phosphite triester and the chloroformate ester at a temperature from 20° to 130° C. and by heating at 80° to 130° C. for 1 to 10 hours, the following compounds were prepared analogously to example 1.

(a) Diethyl 4-chlorophenoxycarbonylphosphonate

From 20 g (0.12 mole) of triethylphosphite and 19.1 g (0.10 mole) of 4-chlorophenyl chloroformate (prepared according to M. J. Zabik and R. D. Scheutz J. Org. Chem. 32 (1967) 300). (125° C., 2 hours). Yield 26.3 g (90%). $Bp_{0.01}$ 153°–6° C., $n_D^{21}$ 1.4980.

Analysis for $C_{11}H_{14}ClO_5P$. Found (calculated): C 44.85 (45.14), H 4.83 (4.82), P 10.54 (10.59).

NMR (CDCl₃) δ: 1.45 (t, CH₃), 4.17–4.63 (CH₂), 7.03–7.48 (aromatic).

(b) Dimethyl p-tolyloxycarbonylphosphonate

From 10.3 g (85 mmole) of trimethylphosphite and 10.3 g (60 mmole) of p-tolyl chloroformate (prepared according to M. J. Zabik and R. D. Schuetz, J. Org. Chem. 32 (1967) 300). (100° C., 2 hours). Yield 93%. $Bp_{0.2}$ 131° C., $n_D^{20}$ 1.4972.

Analysis for $C_{10}H_{13}O_5P$. Found (calculated): C 49.37 (49.18), H 5.53 (5.36), P 11.71 (12.69).

NMR (CDCl₃) δ: 2.40 (CH₃), 3.92 and 4.12 (CH₃O), 6.97–7.37 (aromatic protons).

A second distillation gave a yield of about 80%. New analysis: C 49.13 (49.18), H 5.41 (5.36), P 12.71 (12.69).

(c) Dimethyl 3,4-dichlorophenoxycarbonylphosphonate

From 10.3 g (85 mmole) of trimethylphosphite and 13.5 g (60 mmole) of 3,4-dichlorophenyl chloroformate (100° C., 2 hours). Yield 11.4 g (64%). $Bp_{0.04}$ 164° C., $n_D^{20}$ 1.5271.

Solidifies to colourless crystals m.p. 58°–9° C.

Analysis for $C_9H_9Cl_2O_5P$. Found (calculated). C 36.06 (36.14), H 3.31 (3.03), Cl 23.58 (23.71), P 10.50 (10.36).

NMR (CDCl₃) δ: 3.93 and 4.07 (CH₃O), 7.0–7.6 (aromatic protons).

IR (KBr) $cm^{-1}$: 1740 (CO), 1265, 1200, 1165, 1055, 1020.

(d) Dimethyl 2-adamantoxycarbonylphosphonate

From 1.5 g (12 mmole) of trimethylphosphite and 2.0 g (9.3 mmole) of 2-adamantyl chloroformate: (100°–110° C., 2 hrs). Yield 1.0 g (37%). Bp$_{0.3}$ 160° C.
NMR (CDCl$_3$) δ: 1.5–2.2 (adamant), 3.87 and 4.03 (CH$_3$O), 5.2 (CO$_2$CH).

(e) Dimethyl phenoxycarbonylphosphonate

From 10.0 ml (85 mmole) of trimethylphosphite and 10.0 g (64 mmole) of phenylchloroformate. (100° C., 2 hours). Yield 11.0 g (75%). Bp$_{0.5}$ 125°–7° C. n$_D^{25}$ 1,4907.
NMR (CDCl$_3$) δ: 3.90 and 4.09 (CH$_3$), 7.10–7.60 (C$_6$H$_5$).

(f) Dimethyl 4-(ethoxycarbonyl)phenoxycarbonylphosphonate

From 16.1 g (0.13 mole) of trimethylphosphite and 22.8 g (0.10 mole) of 4-ethoxycarbonylphenyl chloroformate. (100° C., 3 hours). Yield 26.7 g (88%). Bp$_{0.05}$ 205°–7° C.
Analysis for C$_{12}$H$_{15}$O$_7$P. Found (calculated): C 47.70 (47.69), H 5.07 (5.00), P 10.15 (10.25).
NMR (CDCl$_3$) δ: 1.40 (t, J 7 Hz, CH$_3$—C), 4.02 (d, J 11 Hz, CH$_3$O), 4.36 (q, J 7 Hz, CH$_2$), 7.27 and 8.10 (d, J 9 Hz).
IR (neat) cm$^{-1}$: 1740 (CO).

(g) Diethyl 4-(ethoxycarbonyl)phenoxycarbonylphosphonate

From 21.6 g (0.13 mole) of triethylphosphite and 22.8 g (0.10 mole) of 4-ethoxycarbonylphenyl chloroformate. (120° C., 2 hours). Yield 26.1 g (88%). Bp$_{0.01}$ 190°–2° C. n$_D^{25}$ 1.4890.
Analysis for C$_{14}$H$_{19}$O$_7$P. Found (calculated): C 50.77 (50.91), H 6.20 (5.80), P 9.53 (9.38).
NMR (CDCl$_3$) δ: 1.15–1.38 (CH$_3$), 4.15–4.55 (CH$_2$), 7.28 and 8.12 (d, J 9 Hz).

(h) Diphenyl ethoxycarbonylphosphonate

[According to A. Takamizawa and Y. Sato, Chem. Pharm. Bull. 12 (1964) 398]. Yield 97%, Bp$_{0.03}$ 153°–5° C., n$_D^{25}$ 1.5314.

(i) Dimethyl benzyloxycarbonylphosphonate

From 50 ml (0.4 mole) of trimethylphosphite and 56.9 g (0.3 mole) of benzyl chloroformate (Sigma 90–95%) (100° C., 2 hours). Yield 73 g (90%). Bp$_{0.02}$ 135°–6° C. n$_D^{25}$ 1,4997.
NMR (CDCl$_3$) δ: 3.75 and 3.97 (CH$_3$), 5.28 (s, CH$_2$), 7.37 (s, C$_6$H$_5$).

(k) Diethyl methoxycarbonylphosphonate

[According to T. Reetz et al. J. Amer. Chem. Soc. 77 (1955) 3813]. Yield 87%, Bp$_1$ 87°–91° C., n$_D^{22}$ 1.4235.
NMR (CDCl$_3$) δ: 1.20 (t, J 6 Hz, CH$_3$—C), 3.83 (s, CO$_2$CH$_3$), 4.03–4.52 (J 6 Hz, CH$_2$).
IR (neat) cm$^{-1}$: 1725 (CO).

(l) Dimethyl n-butoxycarbonylphosphonate

From 10.0 ml (85 mmole) of trimethylphosphite and 8.7 g (64 mmole) of n-butyl chloroformate. (100° C., 1.5 hours).
Yield 10.9 g (81%). Bp$_{1.0}$ 97°–100° C. n$_D^{25}$ 1,4269.
NMR (CDCl$_3$) δ: 0.80–1.08 (CH$_3$—), 1.15–1.80 (CH$_2$—CH$_2$), 3.80 and 4.02 (CH$_3$O), 4.20–4.41 (OCH$_2$).

(m) Dimethyl i-propoxycarbonylphosphonate

From 10.0 ml (85 mmole) of trimethylphosphite and 7.8 g (64 mmole) of i-propyl chloroformate. (100° C., 2 hours).
Yield 8.0 g (64%). Bp$_2$ 90°–2° C. n$_D^{25}$ 1,4202.
NMR (CDCl$_3$) δ: 1.39 (d, J 6 Hz, C—CH$_3$), 3.80 and 3.98 (CH$_3$O), 5.0–5.4 (CH).

(n) di-n-butyl methoxycarbonylphosphonate

From 26.6 g (0.10 mole) of tri-n-butylphosphite and 18.9 g (0.20 mole) of methyl chloroformate (80° C., 6 hours).
Yield 22.4 g (89%). Bp$_{0.2}$ 85°–105° C., n$_D^{25}$ 1.4310.
NMR (CDCl$_3$) δ: 0.80–1.03 (CH$_3$), 1.18–1.98 (CH$_2$—CH$_2$), 3.85 (s, CO$_2$CH$_3$), 4.23 (q, J 6 Hz, OCH$_2$).

(o) Triethyloxycarbonylphosphonate

[According to P. Nylén, Ber. 57 (1924) 1023]. Yield 85–90%. Bp$_{16}$ 136°–141° C., n$_D^{24}$ 1.4225.

(p) Dimethyl cyclohexoxycarbonylphosphonate

From 24.8 g (0.20 mole) of trimethylphosphite and 32.1 g (0.20 mole) of cyclohexylchloroformate, (Y. Iwakura and A. Nabeya, J. Org. Chem. 25 (1960) 1118; M. E. Fourneau et al. Chem. Abstr. 16 (1922) 240; J. H. Saunders et al. J. Am. Chem. Soc. 73 (1951) 3797). (100° C., 2 hours). Yield 30 g (54%). Bp$_{1.4-1.8}$ 148°–151° C. n$_D^{21}$ 1.4543.
Analysis for C$_9$H$_{17}$O$_5$P. Found (calculated): C 45.97 (45.76), H 7.27 (7.26), P 13.37 (13.12).
NMR (CDCl$_3$) δ: 1.3–2.0 (CH$_2$), 3.83 and 4.03 (CH$_3$), 5.1 (CH).

(q) Dimethyl cyclopentylmethylenoxycarbonylphosphonate

From 12.4 g (0.10 mole) of trimethylphosphite and 16.26 g (0.10 mole) of cyclopentylmethylchloroformate. (100° C., 2 hrs).
Yield 14.4 g (61%). Bp$_{1.5-2.0}$ 150°–4° C., n$_D^{21}$ 1.4549.

(r) Dimethyl ethoxycarbonylphosphonate

From 10,0 ml (85 mmole) of trimethylphosphite and 10.0 ml (105 mmole) of ethyl chloroformate (100° C., 1,5 hours). Yield 12,5 g (80%). Bp$_{15}$ 122° C.
NMR (CDCl$_3$) δ: 1,33 (t, J 7 Hz, CH$_3$—C), 3,88 (d, J 11 Hz, CH$_3$O), 4,36 (quintet, J 7 Hz, CH$_2$—C).
Analysis for C$_9$H$_{17}$O$_5$P. Found (calculated): C 45.80 (45.76), H 7.30 (7.26), P 12.97 (13.11).
NMR (CDCl$_3$) δ: 1.1–2.6 (cyclopentyl), 3.87 and 4.05 (CH$_3$), 4.12 (CH$_2$, d, J 7 Hz).

EXAMPLE 3

Ethyl, p-methoxyphenyl phenoxycarbonylphosphonate 24.4 g (0.10 mole) of diethyl p-methoxyphenylphosphite and 31.2 g (0.20 mole) of phenyl chloroformate were mixed at room temperature and heated 130° C. for about 2 hours. The excess of phenyl chloroformate was evaporated at 130° C. with a vacuum pump, to give the product as a residue.
n$_D^{25}$ 1.5378. NMR (CDCl$_3$) δ: 1.42 (t, J 7 Hz, CH$_3$—C), 3.80 (s, CH$_3$O), 4.50 (quintet, J 7 Hz, CH$_2$), 6.76–7.70 (9H).
IR (neat) cm$^{-1}$: 1740, 1590, 1500, 1180, 980 and 920.

EXAMPLE 4

Analogously as described in example 3, the following compounds were prepared by heating at 20°-130° C. for 2-15 hours.

(a) Ethyl, p-chlorophenyl phenoxycarbonylphosphonate

From 24.9 g (0.10 mole) of diethyl p-chlorophenylphosphite and 31.3 g (0.20 mole) of phenyl chloroformate. (110° C., about 15 hours).

NMR (CDCl$_3$) δ: 1.47 (t, J 7 Hz, CH$_3$—C), 4.50 (quintet, J 7 Hz, CH$_2$), 7.0-7.7 (aromatic).

(b) Ethyl, 3,4-dichlorophenyl phenoxycarbonylphosphonate

From 14.2 g (0.05 mole) of diethyl 3,4-dichlorophenylphosphite and 15.7 g (0.10 mole) of phenyl chloroformate (110° C., about 15 hours).

NMR (CDCl$_3$) δ: 1.46 (t, J 7 Hz, CH$_3$), 4.50 (quintet, J 7 Hz, CH$_2$), 7.0-7.6 (aromatic).

(c) Ethyl, 2,6-dimethylphenyl methoxycarbonylphosphonate

From 20.0 g (83 mmole) of diethyl 2,6-dimethylphenylphosphite and 10.0 ml (127 mmole) of methyl chloroformate. (100° C., 4 hours). Yield 22.2 g (99%). By g.l.c. (3% OV 17 column, 120°-280° C.) only one peak was seen.

NMR (CDCl$_3$) δ: 1.35 (t, J 7 Hz, CH$_3$—C), 2.37 (s, CH$_3$—Ar), 3.92 (s, CO$_2$CH$_3$), 4.40 (quintet, J 7 Hz, CH$_2$), 7.03 (s, C$_6$H$_3$).

An analytical sample was distilled in vacuo. Bp$_{0.04}$ 125°-8° C. n$_D^{25}$ 1.4914.

(d) Ethyl, 5-indanyl methoxycarbonylphosphonate

From 20.0 g (78 mmole) of diethyl 5-indanylphosphite and 10.0 ml (127 mmole) of methyl chloroformate (100° C., 4 hours).

Yield 22 g (99%). By g.l.c. (3% OV17 column, 120°-280° C.) the purity was estimated to be about 85%.

NMR (CDCl$_3$) δ: 1.40 (t, J 7 Hz, CH$_3$—C), 1.85-2.35 (multiplet, CH$_2$), 2.80-3.05 (CH$_2$—C—CH$_2$), 3.82 (s, CO$_2$CH$_3$), 4.42 (quintet, J 7 Hz, CH$_2$O), 6.9-7.3 (C$_6$H$_3$).

(e) Methyl 1-adamantyl methoxycarbonylphosphonate

From 24.4 g (0.1 mole) of dimethyl 1-adamantylphosphite and 18.9 g (0.2 mole) of methyl chloroformate (90° C., 2 hours).

NMR (CDCl$_3$) δ: 1.63 and 2.16 (broad singlets. C$_{10}$H$_{15}$), 3.83 (s, CO$_2$CH$_3$), 3.88 (d, J 12 Hz, OCH$_3$). IR (neat) cm$^{-1}$: 1730, 1290, 1230, 1060, 1020, 990.

An analytical sample was distilled in vauco. B.p.$_{0.01}$, 125°-7°. n$_D^{25}$ 1.4922.

(f) Methyl p-acetylphenyl methoxycarbonylphosphonate

From 11.4 g (50 mmole) of dimethyl p-acetylphenylphosphite and 9.5 g (100 mmole) of methyl chloroformate (100° C., 1 hour and 120° C., 2 hours). n$_D^{25}$ 1.5178.

NMR (CDCl$_3$) δ: 2.60 (s, CH$_3$—CO), 3.92 (s, CO$_2$CH$_3$), 4.08 (d, J 11 Hz, OCH$_3$), 7.39 and 8.03 (doublets, J 9 Hz, C$_6$H$_4$).

IR (neat) cm$^{-1}$: 1730, 1690, 1610, 1510, 1370, 1300, 1270, 1250, 1220, 1050, 950.

(g) Ethyl p-acetylphenyl methoxycarbonylphosphonate

From 12,8 g (50 mmole) of diethyl p-acetylphenylphosphite and 9,5 g (100 mmole) of methylchloroformate (120°, 6 hours) n$_D^{25}$ 1,5152. NMR (CDCl$_3$) δ: 1,41 (t, J 7 Hz, ≡CH$_3$—C), 2,60 (s, CH$_3$—CO), 3,89 (s, CH$_3$—O), 4,45 (quintet, J 7 Hz, CH$_2$), 7.40 and 8,03 (doublets, J 9 Hz, C$_6$H$_4$).

IR (neat) cm$^{-1}$: 1730, 1690, 1600, 1510, 1370, 1290, 1270, 1240, 1210, 1030, 950.

EXAMPLE 5

Dibenzyl ethoxycarbonylphosphonate

Ethanol (4.6 g) was added to a fine suspension of sodium metal (2.25 g) in dry ether (200 ml) under an atmosphere of nitrogen. The mixture was heated for 8 hours, after which dibenzylphosphite (25.7 g) in dry ether (50 ml) was added. After standing over-night the dibenzylphosphite sodium salt was added over a period of 2 hours to a cold solution of ethyl chloroformate (10.8 g) in ether, under an atmosphere of nitrogen. The reaction was heated at reflux for 1 hour, cooled, washed with water, a NaCl solution and dried over Na$_2$SO$_4$. The ether was evaporated. After evaporating and discarding components volatile at 0.01 mm and 150° C. the residue was collected (13 g).

Analysis: NMR (CDCl$_3$): 1.10-1.25 (CH$_3$), 4.03-4.50 (CO$_2$CH$_2$), 5.00-5.32 (CH$_2$), 7.39 (C$_6$H$_5$). IR (neat): 1720 cm$^{-1}$ (CO).

Examples of methods used for the synthesis of haloformate esters.

EXAMPLE 6

3,4-Dichlorophenyl chloroformate 40.75 g (0.25 mole) of 3,4-dichlorophenol in 135 ml of dry toluene was cautiously added to 240 ml (0.46 moles) of a 20% solution of phosgene in toluene. The reaction flask was equipped with a stirrer, a dry ice condensor and a dropping funnel, and the reaction temperature was 20°-25° C. 31.5 g (0.26 moles) of N,N-dimethylaniline was added over a period of 45 min and the flask was left without stirring for 2 hours. The precipitate was filtered off and washed with 2×25 ml of toluene. The combined toluene solutions were cooled on ice and quickly washed with 50 ml of water, 100 ml of 0.1N HCl and 100 ml of water. The solution was dried over magnesium sulfate and evaporated on a rotary evaporator. The residue was distilled in vacuo over a Vigreux column, to give 46.4 g (82%) of 3,4-dichlorophenylchlorformate, bp$_{20}$ 134° C. The product becomes slightly blue and crystallizes in long needles, m.p. 51°-53° C.

EXAMPLE 7

2-Adamantanyl chloroformate 15.2 g (0.10 mole) of 2-adamantanol and 12.1 g (0.10 mole) of N,N-dimethylaniline were dissolved in 200 ml of dry ether and added to 105 ml (0.20 mole) of phosgene in toluene (20%) over a period of 1 hour. The reaction flask was kept at 0° C. and was equipped with a stirrer and a dry ice condensor. The product was stirred at room temperature for another hour, after which the solution was cooled on ice and 10 ml of ice cold water was added carefully. The water and the toluene phases were quickly separated and the toluene was quickly washed with 50 ml of 0.5N HCl, 50 ml of 0.5N NaOH and 50 ml of H$_2$O. The toluene solution was dried over magnesium sulfate and evaporated in vacuo. The residue was dissolved in dry n-hexane and filtered. The hexane was evaporated and the residue was distilled in vacuo to give 2-adamantanyl chloroformate bp$_{15}$ 135° C., n$_D^{19}$ 1.521, IR (CO) 1770 cm$^{-1}$.

EXAMPLE 8

Cyclopentylmethylmethylene chloroformate

A mixture of 24.2 g (0.20 mole) N,N-dimethylaniline and 20.3 g (0.20 mole) of cyclopentylmethanol was slowly added to a 20% solution of phosgene in toluene (104 ml, 0.20 mole) cooled to −5° to +5° C. After the addition the reaction mixture was allowed to attain room temperature and was kept at room temperature for 30 min. The precipitate was filtered off and the solvent was evaporated. Distillation in vacuo gave 26.3 g (81%) of cyclopentylmethyl chloroformate. Bp$_{17-20}$ 82°–84° C., n$_D^{21}$ 1.4541. Analysis for C$_7$H$_{11}$ClO$_2$. Found (calculated): Cl 21.37 (21.80). IR (neat) cm$^{-1}$: 1790 (CO).

EXAMPLE 9

4-Ethoxycarbonylphenyl chloroformate

From 49.9 g (0.3 mole) of 4-hydroxybenzoic acid ethylester, 40 ml (0.3 mole) of N,N-dimethylaniline and 0.4 mole of a 20% solution of phosgene in toluene, 54.4 g (79%) of 4-ethoxycarbonylphenyl chloroformate was obtained. Bp$_{10}$146°–146.5° C., n$_D^{25}$ 1.5140. IR (neat) cm$^{-1}$: 1720 and 1790 (CO).

Examples of methods used for the synthesis of triesters of phosphorous acid.

EXAMPLE 10

Diethyl p-methoxyphenylphosphite

The synthesis was carried out by the method described by W. G. Bentrude, E. R. Hansen, W. A. Khan, T. B. Min and P. E. Rogers, J. Amer. Chem. Soc. 95 2292 (1973) for the preparation of diethyl phenylphosphite.

A solution of 50.0 g (0.364 mole) of phosphorous trichloride in 500 ml of anhydrous ether was stirred (mechanically) under an atmosphere of argon. The temperature was maintained at −20°–−15° C. during the addition of 37.1 g triethylamine, followed by the slow addition of p-methoxyphenol, 45.19 g (0.364 mole) in 200 ml of dry ether over a period of 2.5 hours. When the addition was complete another portion of triethylamine 73.8 g (0.728 mole), was added, followed by the slow addition of absolute ethanol, 33.5 g (0.728 mole), in 50 ml of dry ether (1.5 hours). The mixture was stirred at room temperature over night. The mixture was warmed and allowed to reflux for 1 hour. The triethylamine hydrochloride was filtered off and was washed with dry ether. The solvent was removed under reduced pressure. Distillation of the residual oil yielded 48.6 g of diethyl p-methoxyphenylphosphite, bp$_{110}$ (1.2 mm)–102 (0.6 mm). Another 4.20 g was obtained at 0.2 mm bp 92°–96° C. n$_D^{20}$ 1.4993.

Analysis for C$_{11}$H$_{17}$O$_4$P. Found (calculated). C 54.14 (54.10), H 7.07 (7.02), P 12.74 (12.68).

NMR (CDCl$_3$) δ: 1.26 (t, J 7 Hz, CH$_3$), 3.70 (s, CH$_3$O), 4.00 (quintet, J 7 Hz, CH$_2$), 6.7–7.1 (m, C$_6$H$_4$).

IR (neat) cm$^{-1}$: 2980, 1510, 1220, 1030, 920.

EXAMPLE 11.

Analogously as described in Example 10, the following phosphites were prepared.

(a) Diethyl p-chlorophenylphosphite

Yield 43%. Bp$_{1.5}$ 102°–104° C., n$_D^{25}$ 1.5047.

NMR (CDCl$_3$) δ: 1.17 (t, J 7 Hz, CH$_3$), 4.00 (quintet, J 7 Hz, CH$_2$), 6.9–7.3 (C$_6$H$_4$).

IR (neat) cm$^{-1}$: 2980, 1590, 1490, 1390, 1230, 1030, 920.

(b) Diethyl 3,4-dichlorophenylphosphite

Yield 18%. Bp$_{0.02}$ 110° C., n$_D^{25}$ 1.5188.

Analysis for C$_{10}$H$_{13}$Cl$_2$O$_3$P. Found (calculated): C 42.47 (42.43), H 4.55 (4.63), Cl 25.11 (25.05), P 10.33 (10.94).

NMR (CDCl$_3$) δ: 1.30 (t, J 7 Hz, CH$_3$), 4.03 (quintet; J 7 Hz, CH$_2$), 6.9–7.5 (C$_6$H$_3$).

IR (neat) cm$^{-1}$: 2980, 1590, 1570, 1470, 1390, 1260, 1220, 1120, 1030, 900.

(c) Dimethyl p-acetylphenylphosphite

Yield 20%. Bp$_{0.03}$ 128°–130° C., n$_D^{25}$ 1.5308.

Analysis for C$_{10}$H$_{13}$O$_4$P. Found (Calculated): C 52.36 (52.64), H 5.74 (5.74), P 13.33 (13.57).

NMR (CDCl$_3$) δ: 2.58 (s, CH$_3$CO), 3.68 (d, J 11 Hz, CH$_3$O), 7.14 and 7.97 (d, J 9 Hz).

(d) Dimethyl 1-adamantylphosphite

Yield 50% (crude product).

NMR (CDCl$_3$) δ: 1.63 and 2.0–2.2 (adamantyl), 3.50 (d, J 11 Hz, CH$_3$O).

(e) Diethyl 2,6-dimethylphenylphosphite

Yield 29%. Bp$_{0.01}$ 84°–5° C.

NMR (CDCl$_3$) δ: 1.30 (t, J 7 Hz, CH$_3$—C), 2.33 (s, CH$_3$—Ar), 4.03 (quintet, J 7 Hz, CH$_2$O), 7.00 (s, C$_6$H$_3$).

(f) Diethyl 5-indanylphosphite

Yield 29%. Bp$_{0.01}$ 140° C.

NMR (CDCl$_3$) δ: 1.30 (t, J 7 Hz, CH$_3$), 1.95–2.30 (CH$_2$), 2.97–3.03 (CH$_2$—C—CH$_2$), 4.03 (quintet, J 7 Hz, CH$_2$O), 6.7–7.3 (C$_6$H$_3$).

Preparation of diesters of hydroxycarbonylphosphonic acid.

(g) Diethyl p-acetylphenylphosphite

Yield 21%. Bp$_{0.02}$ 142°–158° C. n$_D^{25}$ 1.5194. NMR (CDCl$_3$) δ: 1.33 (t, J 7 Hz, CH$_3$—C), 2.60 (S, CH$_3$—CO), 4.08 (quintet, J 7 Hz, CH$_2$—C), 7.90 and 8.00 (doublets, J 9 Hz).

EXAMPLE 12

Sodium methyl benzyloxycarbonylphosphonate

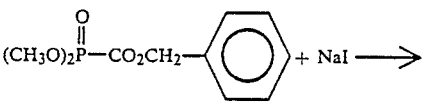

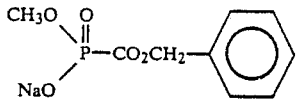

3.66 g of dimethyl benzyloxycarbonylphosphonate and 2.25 g of sodium iodide were stirred in 25 ml of dry tetrahydrofuran for 3 days. The precipitate was filtered, washed with ether and dried in a desiccator. Colourless, hygroscopic crystals of the title compound were obtained (3.15 g, 82%). By t.l.c. (polyethyleneimine, 1M LiCl, molybdate spray) the compound was estimated to contain <0.4% of trisodium oxycarbonylphosphonate.

Analysis for $C_9H_{10}NaO_5P \times \frac{1}{2}H_2O$. Found (calculated): $H_2O$ 1.7% (1.75); Na 8.8% (8.96); Molecular weight by titration 257 (256.6).

NMR ($D_2O$) δ: 3.57 and 2.76 ($CH_3$), 5.28 singlet ($CH_2$), 7.48 singlet ($C_6H_5$).

EXAMPLE 13

Analogously with example 12, the following compounds were prepared by treating the respective triester with sodium iodide. The purification procedure was somewhat modified.

(a) Sodium n-butyl methoxycarbonylphosphonate

From di-n-butyl methoxycarbonylphosphonate (3.78 g). The collected reaction product (1.65 g) was dissolved in water (10 ml) and added to acetone (100 ml). After filtration the solvent was evaporated. The residue was triturated with aceton, centrifuged and dried in a desiccator, to yield colourless crystals (0.46 g, 14%). Thin layer chromatography: Silica gel, eluted with ethanol and visualized with iodine vaper $R_f$ 0.46.

By t.l.c. (polyethyleneimine, 1M LiCl, molybdate spray) the compound was estimated to contain <0.4% of trisodium oxycarbonylphosphonate.

Analysis for $C_6H_{12}NaO_5P$. Found (calculated): Na 10.8% (10.54); Molecular weight (by titration) 218.8 (218.1).

(b) Sodium ethyl ethoxycarbonylphosphonate

From hydroxycarbonylphosphonic acid triethyl ester (3.15 g). The reaction precipitate (0.35 g) was centrifuged, washed with ether, dissolved in water (10 ml) and the water solution was washed with ether. The solution was evaporated in vacuo (3 mm) at room temperature. Ethanol was added to the residue and evaporated. The residue was treated with ether and dried in a desiccator. Colourless crystals (0.29 g, 9%) were obtained. By t.l.c. (polyethyleneimine, 1M LiCl, molybdate spray) the compound was estimated to contain <0.4% of trisodium oxycarbonylphosphonate.

Analysis for $C_5H_{10}NaO_5P$. Found (calculated): Na 11.7% (11.26); Molecular weight (by titration) 204.0 (204.1).

EXAMPLE 14

Sodium phenyl ethoxycarbonylphosphonate

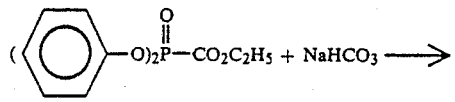

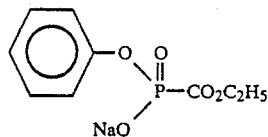

Diphenyl ethoxycarbonylphosphonate (3.06 g) and sodium hydrogencarbonate (0.84 g) were stirred in water (10 ml) at room temperature for about 24 hours. The solvent was evaporated and the residue extracted with ethanol. The ethanol was evaporated and the residue was washed with ether. The residue was recrystallized twice from isopropanol. Colourless crystals (0.67 g, 27%) were obtained.

Thin layer chromatography on silica gel, eluted with ethanol and developed with iodine vapor: $R_f$ 0.66. By t.l.c. the compound was estimated to contain <0.4% of trisodium oxycarbonylphosphonate.

Analysis for $C_9H_{10}NaO_5P$. Found (calculated): C 42.99 (42.87), H 3.73 (4.00), Na 9.12 (9.12), P 12.12 (12.28). Molecular weight by titration 253.8 (252.1).

Reactions involving a trimethylsilyl group:

EXAMPLE 15

Sodium 2,6-dimethylphenyl methoxycarbonylphosphonate 11.1 g (41 mmole) of ethyl 2,6-dimethylphenyl methoxycarbonylphosphonate and 12.7 g (83 mmole) of bromo trimethylsilane were stirred under a nitrogen atmosphere for about 3 days.

Excess of bromotrimethylsilane was evaporated in vacuo (0.5 mm) and 4.62 g (14 mmole) of the residue (total 12.7 g) was added to 60 ml of water and 27.8 g (60 meq.) of Amberlite IRC 50 (Na+). The mixture was stirred for about 2 days, and filtered. The solution was evaporated in vacuo, redissolved in 50 ml of water and washed with ether (3×25 ml). The solution was evaporated in vacuo, the residue was dissolved in 50 ml of ethanol and 200 ml of ether was added. The precipitate was recrystallized twice from i-propanol to give 1.77 g (45%) of the title compound. By t.l.c. (polyethyleneimine, 1M LiCl, molydate spray) the compound was shown to contain <0.4% of trisodium oxycarbonylphosphonate.

Analysis for $C_{10}H_{12}O_5PNa$. Found (calculated): Na 8.64 (9.0).

NMR ($D_2O$) δ: 2.30 (s, $CH_3$—Ar), 3.91 (s, $CO_2CH_3$), 7.12 (s, $C_6H_3$). IR (KBr) cm$^{-1}$: 1730, 1700, 1490, 1260, 1180, 1100, 920.

EXAMPLE 16

Analogously as described in example 15, the following compounds were prepared.

(a) Sodium 5-indanyl methoxycarbonylphosphonate

From ethyl 5-indanyl methoxycarbonylphosphonate. Yield 16%. By t.l.c. (polyethyleneimine, 1M LiCl, molybdate spray) the compound was shown to contain <0.4% of trisodium oxycarbonylphosphonate.

Analysis for $C_{11}H_{12}O_5PNa$. Found (calculated): Na 8.3 (8.3). Equivalent weight by titration: 279.1 (278.2).

NMR ($D_2O$) δ: 1.8–2.3 and 2.7–3.1 ($CH_2$—$CH_2$—$CH_2$), 3.83 (s, $CO_2CH_3$), 6.9–7.4 ($C_6H_3$).

IR (KBr) cm$^{-1}$: 1720, 1500, 1280, 1260, 1210, 1140, 1100, 960.

(b) Sodium 1-adamantyl methoxycarbonylphosphonate

From 11.5 g (0.04 mole) of methyl 1-adamantyl methoxycarbonylphosphonate.

The crude product (11.5 g) was dissolved in 100 ml of warm water, and filtered. The solution was evaporated and the residue was dissolved in 50 ml of water. 400 ml of ethanol was added, the solution was filtered and evaporated in vacuo to give 4.85 g (40%) of the title compound after the residue had been washed with ethanol and dried.

By t.l.c. (polyethyleneimine, 1M LiCl, molybdate spray) the compound was shown to contain <1% of trisodium oxycarbonylphosphonate).

NMR ($D_2O$) δ: 1.50 and 1.85 (broad singlets, $C_{10}H_{15}$), 3.62 (s, $CO_2CH_3$).

Preparation of monoesters of hydroxycarbonylphosphonic acid (of the phosphonic acid group).

EXAMPLE 17

Methyl disodium oxycarbonylphosphonate

The synthesis was carried out analogously by the method described in patent DT-OLS 2435407 (W. Abitz, D. F. Morf and H. A. Brauns).

Dimethyl benzyloxycarbonylphosphonate (6.2 g) in water (50 ml) was stirred and 50% aqueous NaOH (4.0 g) was added dropwise. The mixture was heated at reflux for 1 hour, after which the solution was evaporated in vacuo. The product was redissolved in water (10 ml) and methanol (80 ml) was added slowly. The precipitate was filtered and dried (2.60 g). Later another 0.55 g of the title compound precipitated slowly from the solution in the form of its disodium salt.

By t.l.c. (PEI, 1M LiCl, molybdate spray) the compound was shown to contain <0.5% trisodium oxycarbonylphosphonate.

Analysis for $C_2H_3Na_2O_5P$. Found (calculated): Na 24.9% (24.99); Equivalent weight 92.6 (92.0). (By titration).

NMR ($D_2O$) δ: 3.45 and 3.63 ($CH_3$).

IR (KBr) $cm^{-1}$: 1590 (CO), 1085 (P—O−), 1055 ($POCH_3$).

(b) Ethyl disodium oxycarbonylphosphonate 5.25 g (25 mmole) of triethyl oxycarbonylphosphonate and 50 ml of 1N aqueous NaOH were heated at reflux for 2 hours. The solvent was evaporated, the residue was redissolved in 10 ml of $H_2O$ and 15 ml of ethanol was added. The precipitate was filtered and discarded. Another 40 ml of ethanol was added to the solution. The precipitate was filtered and collected. 1.5 g (30%). NMR ($CDCl_3$) δ: 1.25 (t, J 7 Hz, $CH_3$), 3.95 (quintet, J 7 Hz, $CH_2$).

EXAMPLE 18

1-Adamantyl disodiumoxycarbonylphosphonate 11.5 g (0.04 mole) of methyl 1-adamantyl methoxycarbonylphosphonate and 12.5 g (0.08 mole) of bromotrimethylsilane were stirred under a nitrogen atmosphere, at room temperature overnight. Excess of bromotrimethylsilane was evaporated in vacuo (about 0.3 mm) at 50° C. The residue was stirred with 80 ml (0.08 mol) of 1N aqueous NaOH at room temperature for two hours, after which the solvent was evaporated in vacuo.

The residue (12.06 g) was dissolved in 150 ml of water, filtered and 350 ml of ethanol was added to the solution. The precipitate was filtered off (5.47 g), redissolved in 100 ml of water and 60 ml of ethanol was added. The new precipitate (A) was filtered off (2.83), and another 350 ml of ethanol was added to the solution to give another 2.15 g of precipitate (B). Precipitate B was redissolved in 50 ml of water; 20 ml of ethanol was added and the precipitate was discarded. Another 400 ml of ethanol was added, the precipitate was collected by centrifugation, to give, after drying, 1.49 g of the title compound. By performing twice this purification scheme on precipitate A, another 1.92 g of the title compound could be collected.

Both fractions could by t.l.c. (polyethyleneimine, 1M LiCl, molybdate spray) be estimated to contain <1% of trisodium oxycarbonylphosphonate. $R_f$ (the same system) 0.57 single spot.

NMR ($D_2O$) δ: 1.50 and 1.93 (broad singlets). IR (KBr) $cm^{-1}$: 1580 (CO), 1380, 1240, 1200, 1090, 1060, 990.

Preparation of monoesters of the carboxylic group of hydroxycarbonylphosphonic acid.

EXAMPLE 19

Disodium ethoxycarbonylphosphonate 1.20 g (5.7 mmole) of triethyl oxycarbonylphosphonate and 2.65 g (17.2 mmole) of bromotrimethylsilane were stirred at room temperature in a dried flask under an atmosphere of argon. After about 3 hours, volatile components were evaporated in vacuo (1 mm) and the residue was added to 16 g of Amberlite IRC 50 ($Na^+$, 1.3 meq/g) in 25 ml of water. After 1.5 hours the ion exchanger was added to a column and eluted with another 25 ml of water. The combined water phases (50 ml) were washed with diethyl ether, filtered and evaporated in vacuo (3 mm Hg) at room temperature. The residue was washed with ethanol, filtered and dried in a desiccator, to yield 1.88 (88%) of colourless crystals of the title product.

T.l.c. (polyethyleneimine, 1.4M LiCl, molybdate spray): $R_f$ 0.58.

By t.l.c. (1M LiCl) the compound was estimated to contain <0.4% of trisodium oxycarbonylphosphonate.

Analysis for $C_3H_5Na_2O_5P \times 5H_2O$. Found (calculated): $H_2O$ 11.8 (12.0), Na 20.7 (20.4). Molecular weight by titration: 232 (225).

NMR ($D_2O$) δ: 1.23 (t, J 7 Hz, $CH_3$), 4.18 (quartet, J 7 Hz, $CH_2$).

EXAMPLE 20

Analogously as described in example 19, the following reactions and analyses were performed.

(a) Disodium n-butoxycarbonylphoshonate

From dimethyl n-butoxycarbonylphosphonate. Yield 92%. T.l.c. $R_f$ 0.52. By t.l.c. (1M LiCl) compound was estimated to contain <0.5% of trisodium oxycarbonylphosphonate.

Analysis for $C_5H_9Na_2O_5P \times 1.5H_2O$. Found (calculated): $H_2O$ 10.6 (10.7), Na 18.7 (18.2). Molecular weight 262 (253).

NMR ($D_2O$) δ: 0.9 ($CH_3$), 1.2–1.8 ($CH_2$—$CH_2$), 4.1 ($OCH_2$).

(b) Disodium i-propoxycarbonylphosphonate

From dimethyl i-propoxycarbonylphosphonate. Yield 90%. T.l.c. $R_f$ 0.53. By t.l.c. (1M LiCl) the compound was estimated to contain <0.4% of trisodium oxycarbonylphosphonate.

Analysis for $C_4H_7Na_2O_5P \times 1.5H_2O$. Found (calculated): $H_2O$ 11.6 (11.3), Na 19.1 (19.2). Molecular weight: 234 (239).

NMR ($D_2O$) δ: 1.20 (d, J 6 Hz, $CH_3$), 4.93 (m, CH).

(c) Disodium benzyloxycarbonylphosphonate

From dimethyl benzoxycarbonylphosphonate. Yield 88%. T.l.c. $R_f$ 0.37. By t.l.c. (1M LiCl) the compound was estimated to contain <0.4% of trisodium oxycarbonylphosphonate.

Analysis for $C_8H_7Na_2O_5P \times 1.5H_2O$. Found (calculated): $H_2O$ 9.2 (9.4), Na 16.4 (16.0).

NMR ($D_2O$) δ: 5.14 (s, $CH_2$), 7.37 (s, $C_6H_5$).

(d) Disodium cyclohexoxycarbonylphosphonate

From dimethyl cyclohexoxycarbonylphosphonate. The crude product was purified by precipitation with ethanol from a water solution. Yield 87%. T.l.c. $R_f$0.54. Single spot. By t.l.c. the compound was estimated to contain <0.5% of trisodium oxycarbonylphosphonate.

NMR ($D_2O$) δ: 1.2–2.0 (m, $C_6H_{11}$). IR(KBr) $cm^{-1}$: 1670 (CO), 1120 and 990 ($PO_4{}^{3-}$).

(e) Disodium cyclopentylmethylenoxycarbonylphosphonate

From dimethyl cyclopentylmethylenoxycarbonylphosphonate. The crude product was purified by precipitation with ethanol from a water solution. Yield 67%. T.l.c. $R_f$0.55. Single spot. By t.l.c. the compound was estimated to contain <0.5% of trisodium oxycarbonylphosphonate.

NMR ($D_2O$) δ: 1.1–1.19 [m, $(CH_2)_4$], 2.0–2.3 (m, CH), 3.98 (d, J 7 Hz, $CO_2CH_2$).

IR (KBr) $cm^{-1}$: 1680 (CO), 1130 and 1000 ($PO_4{}^{3-}$).

(f) Disodium 2-adamantoxycarbonylphosphonate

From dimethyl 2-adamantoxycarbonylphosphonate. Yield 80%. T.l.c. $R_f$0.56. Single spot. By t.l.c. the compound was estimated to contain <1% of trisodium oxycarbonylphosphonate.

NMR ($D_2O$) δ: 1.43–2.20 ($C_{10}H_{14}$), 4.93 ($CO_2CH$). IR (KBr) $cm^{-1}$: 1680 (CO), 1120 and 980 ($PO_4{}^{3-}$).

Pharmaceutical compositions

The following examples illustrate the preparation of pharmaceutical compositions of the invention. The active substance in case it can form salts, is preferably used in the form of its sodium salt.

EXAMPLE 21

Aerosol for inhalation

| | |
|---|---|
| Active substance | 1.00 g |
| Miglyol ® | 0.20 g |
| Frigen ® 11/12/113/114 | ad 100.0 g |

EXAMPLE 22

Tablets

| Each tablet contains: | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

EXAMPLE 23

Suppositories

| Each suppository contains: | |
|---|---|
| Active substance | 20.0 mg |
| Ascorbyl palmitate | 1.0 mg |
| Suppository base (Imhausen H or Witespol ® H) | ad 2000.0 mg |

EXAMPLE 24

Syrup

| | |
|---|---|
| Active substance (as its sodium salt) | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

EXAMPLE 25

Injection solution

| | |
|---|---|
| Active substance (as its sodium salt) | 0.500 mg |
| Sodium pyrosulfite | 0.500 mg |
| Disodium edetate | 0.100 mg |
| Sodium chloride | 8.500 mg |
| Sterile water for injection | ad 1.00 ml |

EXAMPLE 26

Inhalation solution

| | |
|---|---|
| Active substance | 5.00 g |
| Sodium pyrosulfite | 0.10 g |
| Disodium edetate | 0.10 g |
| Sodium chloride | 0.85 g |
| Purified water | ad 100.0 ml |

EXAMPLE 27

Sublingual tablets

| | |
|---|---|
| Active substance | 5.0 mg |
| Lactose | 85.0 mg |
| Talc | 5.0 mg |
| Agar | 5.0 mg |
| | 100.0 mg |

EXAMPLE 28

Drops

| | |
|---|---|
| Active substance | 2.00 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.0 ml |

EXAMPLE 29

Syrup

| | |
|---|---|
| Active substance | 0.200 g |
| Liquid glucose | 30.0 g |
| Sucrose | 50.0 g |
| Ascorbic acid | 0.1 g |
| Disodium edetate | 0.01 g |
| Orange essence with solubilizer | 0.25 g |
| Hydrochloric acid to pH 6.0–8.0 | |
| Purified water | ad 100.0 g |

EXAMPLE 30

Solution for injection

| | |
|---|---|
| Active substance | 0.500 mg |
| Disodium edetate | 0.100 mg |
| Sodium chloride for isotonia q.s. | |
| Hydrochloric acid to pH 6.5–8.0 | |
| Starile water for injection | ad 1.00 ml |

EXAMPLE 31

Solution for inhalation

| | |
|---|---|
| Active substance (as its sodium salt) | 5.00 g |
| Disodium edetate | 0.10 g |
| Sodium chloride | 0.85 g |
| Hydrochloric acid to pH 6.0–8.0 | |
| Purified water | ad 100.0 ml |

EXAMPLE 32

Drops

| | |
|---|---|
| Active substance (as its sodium salt) | 2.00 g |
| Citric acid | 1.00 g |
| Disodium edetate | 0.10 g |
| Liquid glucose | 50.00 g |
| Ethanol 95% | 10.00 g |
| Sodium hydroxide and hydrochloric acid to pH 6.2–6.8 | |
| Purified water | ad 100.0 ml |

EXAMPLE 33

Solution for topical use

| | |
|---|---|
| Active substance (as its sodium salt) | 2.00 g |
| Isopropanol | 38.0 g |
| Glycerol | 13.6 g |
| Hydrochloric acid to pH 5.0–8.5 | |
| Purified water | ad 100.0 g |

Preparations containing 0.2, 0.5 and 1.0 g of active substance.

EXAMPLE 34

Jelly

| | |
|---|---|
| Active substance (as its sodium salt) | 4.0 g |
| Methocel ® | 4.0 g |
| Methyl paraoxybenzoate | 0.12 g |
| Propyl paraoxybenzoate | 0.05 g |
| Sodium hydroxide and hydrochloric acid to pH 6.6–8.5 | |
| Distilled water | ad 100.0 ml |

EXAMPLE 35

Ointment I

| | |
|---|---|
| Active substance (as its sodium salt) | 2.5 g |
| Cetyltrimethylammonium bromide | 0.6 g |
| Stearyl alcohol | 2.25 g |
| Cetanol | 6.75 g |
| Liquid paraffine | 17.0 g |
| Glycerol | 12.0 g |
| Hydrochloric acid to pH 6.0–8.5 | |
| Distilled water | ad 100.0 g |

Preparations containing 0.2, 0.5, 1.0 and 2.0 g of active substance have also been prepared.

EXAMPLE 36

Ointment II

| | |
|---|---|
| Active substance (as its sodium salt) | 2.5 g |
| Polyethylene glycol 1500 | 50.0 g |
| Polyethylene glycol 4000 | 15.0 g |
| Propylene glycol | ad 100.0 g |

EXAMPLE 37

Ointment III

| | |
|---|---|
| Active substance (as its sodium salt) | 3.0 g |
| Sorbitan monoleate | 5.0 g |
| Petrolatum | ad 100.0 g |

EXAMPLE 38

Gastric juice-resistant tablets

Tablets according to Example 22 are coated with an enteric coating solution with the following composition:

| | |
|---|---|
| Cellulose acetate phtalate | 120.0 g |
| Propylene glycol | 30.0 g |
| Sorbitan monoleate | 10.0 g |
| Ethanol 95% | 450.0 ml |
| Acetone | q.s. ad 1000.0 ml |

The coating is carried out by a pouring procedure in a conventional coating pan or by spraying the tablets in a pan spray tablet coater.

EXAMPLE 39

Eye drops

| | |
|---|---|
| Active substance (as sodium salt) | 0.1 g |
| Disodium edetate | 0.10 g |
| Sodium chloride for isotonia q.s. | |
| Hydrochloric acid to pH 6.5–8.0 | |
| Methocel ® 65 HG 4000 | 0.65 |
| Sterile water | ad 100 ml |

EXAMPLE 40

Eye drops

| | |
|---|---|
| Active substance (as sodium salt) | 1.0 g |
| Disodium edetate | 0.10 g |
| Sodium chloride for isotononia q.s. | |
| Hydrochloric acid to pH 6.5–8.0 | |
| Methocel ® 65 HG 4000 | 0.65 |
| Sterile water | ad 100 ml |

EXAMPLE 41

Eye Ointment

| | |
|---|---|
| Active substance (as its sodium salt) | 5 g |
| Paraffin oil | 19 g |
| Petrolatum | 76 g |

EXAMPLE 42

Cream

| | |
|---|---|
| Active substance | 3.0 g |
| Arlaton ® | 4.0 g |
| Cetanol | 2.0 g |
| Stearic acid | 2.0 g |
| Paraffin oil | 2.0 g |
| Propylene glycol | 2.0 g |
| Glycerol | 1.5 g |
| Methyl-p-hydroxybensoate | 0.06 g |
| Propyl-p-hydroxybensoate | 0.03 g |
| Sodium hydroxide | 0.002 g |
| Hydrochloric acid 2 M to pH 8.0 (water phase) | |
| Distilled water | ad 100 g |

EXAMPLE 43

Jelly

| | |
|---|---|
| Active substance | 3.0 g |
| Methocel ® | 2.45 g |
| Glycerol | 10.0 g |
| Tween ® | 0.10 g |
| Methyl-p-hydroxybensoate | 0.06 g |
| Propyl-p-hydroxybensoate | 0.03 g |
| Sodiumhydroxid | 0.002 g |
| Hydrochloric acid 2 M to pH 8.0 | |
| Distilled water | ad 100 g |

Biological tests

I. Inhibition of virus multiplication in cell culture

A. Inhibition of herpes simplex type 1 plaque

The plaque reduction assay for herpes simplex type 1 was performed on GMK (Green Monkey Kidney) cells as described by Ejereito et al. J. Gen. Virol. 2 (1968) 357. Monolayers on 5 cm petri dishes were used and after virus adsorption the test compound was added in the medium. The results are shown below.

Inhibition of herpes simplex type 1 plaque on GMK monolayers

Test compound:

$$\begin{array}{c} R_1-O \quad O \quad O \\ \phantom{R_1-O}\searrow \| \quad \| \\ \phantom{R_1-OOO}P-C-OR_3 \\ R_2-O \end{array}$$

| $R_1$ | $R_2$ | $R_3$ | Code | Conc. of test compound (μm) | Inhibition (%) |
|---|---|---|---|---|---|
| Na | Na | 2-adamantyl | VIS 131 | 500 | 76; 0; ~50 |
| Na | Na | 2-adamantyl | VIS 131 | 100 | 40 |
| C6H5– | C6H5– | C2H5 | VIS 035 | 500 | 74; 0; >90 |
| C2H5 | C2H5 | 4-CH3O-C6H4– | VIS 236 | 500 | 82 |
| CH3 | CH3 | 4-(CH3CH2COO)-C6H4– | VIS 243 | 500 | 56 |
| C2H5 | 4-CH3O-C6H4–CH2– | C6H5– | VIS 057 | 500 | 90 |
| Na | indanyl | CH3 | VIS 441 | 500 | 98 |

-continued

Test compound $$R_1-O \diagdown \underset{R_2-O}{\overset{O}{\underset{\|}{P}}}-\overset{O}{\underset{\|}{C}}-OR_3$$

| $R_1$ | $R_2$ | $R_3$ | Code | Conc. of test compound (μm) | Inhibition (%) |
|---|---|---|---|---|---|
| Na | (indanyl) | $CH_3$ | | 100 | >90 |

B. Inhibition of influenza (WSN Wilson Smith Neurotropic type A.) plaque

The method for plaque assay of influenza has been described by Bentley et. al, Archiv für die Gesamte Virusforschung 33 (1971) 234.

Monolayers of MDCK (Madin Darby Canine Kidney) cells on 5 cm plastic petri dishes were inoculated with 100 plaque-forming units of influenza virus (WSN). After virus adsorption, 5 ml of agarose overlay containing different concentrations of the test compound were added and the plates were incubated at 34° C. for 4 days. The plaques formed at this time were counted. The results are shown below.

Inhibition of influenza (WSN Wilson Smith Neurotropic type A) plaque on GMK monolayers.

(v/v) isopropanol 10% (v/v) glycerol and 45% water (v/v) or 10% glycerol, 0.1% tween, water twice daily for 4 days starting 4 or 24 hours after infection. The appearance of an infected treated area and a similar infected untreated (only isopropanol-glycerol-water) area was scored daily on a scale from 0 to 3. The total effect is judged from the score at day 5.

Test compound $$R_1-O \diagdown \underset{R_2-O}{\overset{O}{\underset{\|}{P}}}-\overset{O}{\underset{\|}{C}}-OR_3$$

| $R_1$ | $R_2$ | $R_3$ | Code | Score at day 5 treated | untreated |
|---|---|---|---|---|---|
| Na | $CH_3$ | Na | VIS 018 | 0 | 3 (1) |
| 1-ada- mantyl | Na | Na | VIS 078 | 1 | 3 (2) |

(1) Start of treatment 4 h after infection
(2) Start of treatment 24 h after infection Test compound $$R_1-O \diagdown \underset{R_2-O}{\overset{O}{\underset{\|}{P}}}-\overset{O}{\underset{\|}{C}}-OR_3$$

| $R_1$ | $R_2$ | $R_3$ | Code | Conc. of test compound (μm) | Inhibition (%) |
|---|---|---|---|---|---|
| $C_2H_5$ | $C_2H_5$ | $CH_3O-C_6H_4-$ | VIS 236 | 500 | 69 |
| $CH_3$ | $CH_3$ | $C_6H_5-$ | VIS 416 | 500 | 68 |
| $CH_3$ | $CH_3$ | $CH_3CH_2OOC-C_6H_4-$ | VIS 243 | 500 | 73 |
| $C_2H_5$ | $C_2H_5$ | $CH_3CH_2OOC-C_6H_4-$ | VIS 241 | 500 | 90; 66 |
| Na | (indanyl) | $CH_3$ | VIS 441 | 500 | 75 |

II. Inhibition of cutaneous herpes on guinea pigs

The effect on cutaneous herpes simplex type 1 infections have been measured in a guinea pig model described by Hubler et al. J. Invest. Dermatol. 69 (1974) 92. The compounds have been tested as topical applications of 30 μl of 2% solution of the compound in 45%

III. Stability test

The acid stability was investigated by dissolving 5 mg of each compound in 1 ml of 0.1N HCl in a test tube. For use as references 0.2 ml of each solution was withdrawn, immediately treated with 0.2 ml of a 10% aqueous solution of $NaHCO_3$ and frozen. The remaining 0.8 ml of each solution was incubated at 37° C. for 2 hours. After incubation, 0.8 ml of a 10% aqueous solution of $NaHCO_3$ was added to each solution and the solutions were frozen. The incubated compounds and the reference compounds were lyophilized to dryness and redissolved in distilled $H_2O$, 0.2 ml and 1.0 ml respectively, for each reference solution and incubated solution. The solutions were applied to silica gel (Merck $PF_{254}$, 20×20 cm) and polyethylene imine (Macherey-Nagel PEI, 20×20 cm) thin layer plates. A total of 20 μl of the reference solutions (100 μg compound) and 25 μl of the incubated solutions (100 μg compound) were applied. To each plate was also added, as references, solutions of phosphorous acid ($H_2HPO_3$) (5 and 20 μg) and of trisodiumphosphonoformate (5 and 20 μg). (Decomposition of phosphonoformic acid at low pH produces phosphorous acid).

The silica gel plates were prepared in duplicate and eluted with a solution composed of methanol—10% aq ammonia-trichloroacetic acid-water (50-15-5-3, v/v) and the polyethylene imine plates were eluted with a 1M aq lithium chloride solution. After elution the plates were dried. One of the duplicated silica gel plates was sprayed with 4% aq $(NH_4)_2MoO_4$ and the polyethylene imine plates were sprayed with a solution composed of 60% $HClO_4$—0.1N aq HCl—4% aq $(NH_4)_2MoO_4$—$H_2O$ (5-10-25-60, v/v). The silica gel plates were briefly dried at 80°-90° C. and sprayed with 1% $SnCl_2$ in 10% aq HCl. Phosphorous acid and phosphonic acid groups appeared as blue spots on the silica gel plates (System 1) and as white spots on the polyethylene imine plates (System II). The remaining duplicate silica gel plates were exposed to iodine vapor for detection of di- and triesters of phosphonoformic acid.

|  | $R_f$ System I | $R_f$ System II |
|---|---|---|
| Phosphorous acid | 0.31 | 0.71 |
| $Na_3$—phosphonoformate | 0 | 0.21 |

The formation of phosphorous acid and phosphonoformic acid in each incubated solution was estimated and the results are given below. The figures for the non-incubated reference compounds are given in parenthesis.

Test Compound $$\begin{array}{c} R_1O \\ \phantom{R_1O}\diagdown \\ \phantom{R_1O}P-C-OR_3 \\ \phantom{R_1O}\diagup \phantom{OO} \\ R_2O \phantom{OO} \end{array}$$

| $R_1$ | $R_2$ | $R_3$ | Code | Estimated formation of phosphorous acid (μg) | $Na_3$—phosphonoformate (μg) |
|---|---|---|---|---|---|
| Na | Na | –CH$_2$–C$_6$H$_5$ | VIS 409 | N.D. (N.D.) | N.D. (N.D.) |
| Na | $C_2H_5$ | $C_2H_5$ | VIS 414 | N.D. (N.D.) | N.D. (N.D.) |
| Na | n-$C_4H_9$ | $CH_3$ | VIS 047 | N.D. (N.D.) | N.D. (N.D.) |
| Na | $CH_3$ | –CH$_2$–C$_6$H$_5$ | VIS 406 | N.D. (N.D.) | N.D. (N.D.) |
| $C_2H_5$ | $C_2H_5$ | $C_2H_5$ | EHB 783 | N.D. (N.D.) | N.D. (N.D.) |
| $C_2H_5$ | $C_2H_5$ | $CH_3$ | VIS 224 | N.D. (N.D.) | N.D. (N.D.) |
| n-$C_4H_9$ | n-$C_4H_9$ | $CH_3$ | VIS 046 | N.D. (N.D.) | N.D. (N.D.) |
| $CH_3$ | $CH_3$ | n-$C_4H_9$ | VIS 415 | N.D. (N.D.) | N.D. (N.D.) |
| $CH_3$ | $CH_3$ | $C_6H_5$ | VIS 416 | N.D. (N.D.) | N.D. (N.D.) |
| $CH_3$ | $CH_3$ | –CH$_2$–C$_6H_5$ | VIS 405 | N.D. (N.D.) | N.D. (N.D.) |
| $C_6H_5$– | $C_6H_5$– | $C_2H_5$– | VIS 035 | N.D. (N.D.) | N.D. (N.D.) |
| $CH_3$ | $CH_3$ | i-$C_3H_7$ | VIS 419 | N.D. (N.D.) | N.D. (N.D.) |
| Na | $CH_3$ | Na | VIS 018 | N.D. (N.D.) | N.D. (N.D.) |

-continued

| Test Compound $\begin{array}{c} R_1O \\ \phantom{R_1}\diagdown \\ \phantom{R_1O}P-C-OR_3 \\ \phantom{R_1}\diagup \\ R_2O \end{array}$ | | | | Estimated formation of | |
|---|---|---|---|---|---|
| | | | | phosphorous acid | $Na_3$—phosphonoformate |
| $R_1$ | $R_2$ | $R_3$ | Code | (μg) | (μg) |
| Na | Na | Na | EHB 776 | 20 (N.D.) | |

N.D. = Not detectable (much less than 5 μg)

IV. In vivo metabolization

Metabolization of compounds of the invention was tested in NMR I 19–20 g male mice. The test compound (10 μmol) was dissolved in 0.5 ml saline and injected intraperitoneally. Two mice kept in one cage (for metabolization experiment) were used for each compound. The urine obtained from the two mice on day 1, 2 and 3 after the injections was collected. The urine was diluted with Tris-HCl buffer (pH 7.9) to a constant volume of 1 ml. This volume was then diluted 1:500, 1:5000 and 1:50000 with the same buffer and assayed for phosphonoformic acid activity on cell-free influenza polymerase. The assay mixture which includes $Mn^{2+}$ and assay conditions are described by Bishop, Obijeski and Simpson, J. Virol. 8, 66 (1971). Phosphonoformic acid in diluted urine gave 50% inhibition at 0.5 μM in this assay and was used as a standard to estimate the amount of phosphonoformic acid activity formed in the urine from compounds of the invention.

| Test compound | Recovered phosphonoformic acid activity in urine (μmol phosphonoformic acid) | | |
|---|---|---|---|
| | Day 1 | Day 2 | Day 3 |
| $\begin{array}{c} O\ \ \ O \\ \|\ \ \ \| \\ NaO-P-C-O-(2\text{-adamantyl}) \\ \| \\ ONa \end{array}$ VIS 131 | 0.05 | 0.05 | 0.40 |
| $\begin{array}{c} O\ \ \ O \\ \|\ \ \ \| \\ NaO-P-C-ONa\ (\text{reference}) \\ \| \\ ONa \end{array}$ | 1.25 | 0.13 | <0.01 |

Acute toxicity

A preliminary acute toxicity test was carried out in mice. Groups of two male mice of the NMR I strain weighing 20–21 g received the test compound in doses of 62.5–500 mg/kg i.p. The compound was given as a solution in 0.9% NaCl. The number of animals dead 24 hrs after injection was as follows.

| Test compound | Dose mg/kg i.p. | No of animals dead / No of animals injected |
|---|---|---|
| $\begin{array}{c} NaO\ \ \ O\ \ \ O \\ \phantom{NaO}\diagdown\|\ \ \ \| \\ \phantom{NaO}P-C-OC_2H_5 \\ \phantom{NaO}\diagup \\ Ph-O \end{array}$ VIS 036 | 62.5 | 0/2 |
| | 125 | 0/2 |
| | 250 | 0/2 |
| | 500 | 0/2 |
| $\begin{array}{c} CH_3O\ \ \ O\ \ \ O \\ \phantom{CH_3O}\diagdown\|\ \ \ \| \\ \phantom{CH_3O}P-C-O-Ph \\ \phantom{CH_3O}\diagup \\ CH_3O \end{array}$ VIS 416 | 62.5 | 0/2 |
| | 125 | 0/2 |
| | 250 | 0/2 |
| | 500 | 0/2 |
| $\begin{array}{c} Ph-O\ \ \ O\ \ \ O \\ \phantom{Ph-O}\diagdown\|\ \ \ \| \\ \phantom{Ph-O}P-C-OC_2H_5 \\ \phantom{Ph-O}\diagup \\ Ph-O \end{array}$ VIS 035 | 62.5 | 0/2 |
| | 125 | 0/2 |
| | 250 | 0/2 |
| | 500 | 1/2 |

Discussion of test results

As seen in test I compounds of the invention are active on herpes virus and influenza virus multiplication in cells. As seen in test II compounds of the invention are also active on cutaneous herpes in the guinea pig. According to the stability test III, compounds of the invention are more stable than trisodium phosphonoformate in 0.1M aqueous HCl, which is a model for stability in gastric juice, and the compounds of the invention should therefore be more suitable for oral administrations than phosphonoformic acid and physiologically acceptable salts thereof. The test on in vivo metabolism IV shows that compounds of the invention are metabolized to phosphonoformic acid measured as phosphonoformic acid activity on influenza polymerase. It is also shown in test IV that compounds according to the invention can give such an active metabolite in the urine of mice over a longer time period than trisodium phosphonoformate. Thus compounds of the invention have a prolonged activity in comparison with phosphonoformic acid and its physiologically acceptable satls. The acute toxicity test shows that compounds of the invention have a low acute toxicity, i.e. high LD50 values. In conclusion compounds of the invention have antiviral effects on herpes and influenza viruses and low toxicity. Furthermore compounds of the invention can be biotransformed to phosphonoformic acid or ionized forms thereof which have strong activities against viral functions and virus multiplication.

We claim:

1. A method for treatment of viral infections in animals including man, comprising administering to an animal so infected a compound of the formula

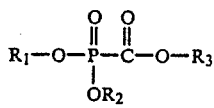

(I)

wherein $R_1$ is selected from the group consisting of hydrogen, alkyl containing 1–6 carbon atoms, cycloalkyl containing 3–6 carbon atoms, cycloalkyl-alkyl containing 4–6 carbon atoms, 1-adamantyl, 2-adamantyl and benzyl; $R_2$ is hydrogen and $R_3$ is selected from the group containing hydrogen and benzyl, provided that when $R_3$ is H, then $R_1$ is alkyl, cycloalkyl or cycloalkyl-alkyl as defined above, or 1-adamantyl, 2-adamantyl or benzyl, or a physiologically acceptable salt or an optical isomer thereof in an amount sufficient for treating said viral infections.

2. A method according to claim 7, wherein the virus is selected from the group consisting of herpes virus, influenza virus and hepatitis B virus.

3. A method for the treatment of viral infections in animals including man, by inhibiting the activity of viral polymerase, comprising administering to an animal so infected a compound of the formula

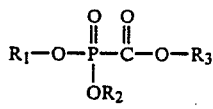

(I)

wherein $R_1$ is selected from the group consisting of hydrogen, alkyl containing 1–6 carbon atoms, cycloalkyl containing 3–6 carbon atoms, cycloalkyl-alkyl containing 4–6 carbon atoms, 1-adamantyl, 2-adamantyl and benzyl; $R_2$ is hydrogen and $R_3$ is selected from the group containing hydrogen and benzyl, provided that when $R_3$ is H, then $R_1$ is alkyl, cycloalkyl or cycloalkyl-alkyl as defined above, or 1-adamantyl, 2-adamantyl or benzyl, or a physiologically acceptable salt or an optical isomer thereof in an amount sufficient for inhibiting the activity of said viral polymerase.

4. A method for inhibiting the activity of viral reverse transcriptase in animals including man, comprising administering to an animal in need of such treatment a compound of the formula

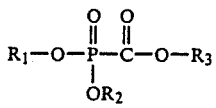

(I)

wherein $R_1$ is selected from the group consisting of hydrogen, alkyl containing 1–6 carbon atoms, cycloalkyl containing 3–6 carbon atoms, cycloalkyl-alkyl containing 4–6 carbon atoms, 1-adamantyl, 2-adamantyl and benzyl; $R_2$ is hydrogen and $R_3$ is selected from the group containing hydrogen and benzyl, provided that when $R_3$ is H, then $R_1$ is alkyl, cycloalkyl or cycloalkyl-alkyl as defined above, or 1-adamantyl, 2-adamantyl or benzyl, or a physiologically acceptable salt or an optical isomer thereof in an amount sufficient for inhibiting the activity of said reverse transcriptase.

5. A method for inhibiting the growth of virus-transformed cells in animals including man, comprising administering to an animal in need of such treatment a compound of the formula

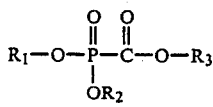

(I)

wherein $R_1$ is selected from the group consisting of hydrogen, alkyl containing 1–6 carbon atoms, cycloalkyl containing 3–6 carbon atoms, cycloalkyl-alkyl containing 4–6 carbon atoms, 1-adamantyl-2-adamantyl and benzyl; $R_2$ is hydrogen and $R_3$ is selected from the group containing hydrogen and benzyl, provided that when $R_3$ is H, then $R_1$ is alkyl, cycloalkyl or cycloalkyl-alkyl as defined above, or 1-adamantyl-2-adamantyl or benzyl, or a physiologically acceptable salt or an optical isomer thereof in an amount sufficient for inhibiting said growth.

6. A method as in any of claims 1, 3, 4 or 5 wherein, in the compound of the formula I, the radicals $R_1$ and $R_2$ are hydrogen and $R_3$ is benzyl.

7. A method as in any of claims 1, 3, 4 or 5 wherein the compound is in the form of its sodium salt.

* * * * *

UNITED STATES PATENT AND TRADEMARK OFFICE
CERTIFICATE OF CORRECTION

PATENT NO. : 4,591,583  Page 1 of 6
DATED : May 27, 1986
INVENTOR(S) : Ake J. E. Helgstrand et al It is certified that error appears in the above-identified patent and that said Letters Patent is hereby corrected as shown below:

First page, third line of ABSTRACT,

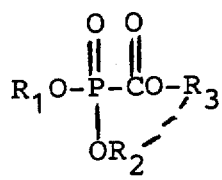

should read

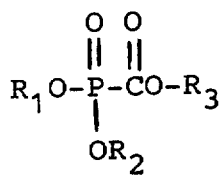

UNITED STATES PATENT AND TRADEMARK OFFICE
CERTIFICATE OF CORRECTION

PATENT NO. : 4,591,583

DATED : May 27, 1986

INVENTOR(S) : Ake J. E. Helgstrand et al

It is certified that error appears in the above-identified patent and that said Letters Patent is hereby corrected as shown below:

First page, line 10 of ABSTRACT,

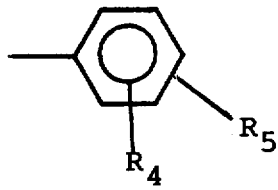

should read

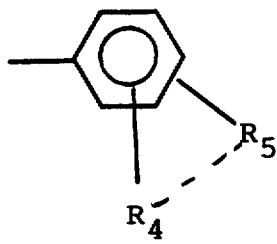

UNITED STATES PATENT AND TRADEMARK OFFICE
CERTIFICATE OF CORRECTION

PATENT NO. : 4,591,583

DATED : May 27, 1986

INVENTOR(S) : Ake J. E. Helgstrand et al

It is certified that error appears in the above-identified patent and that said Letters Patent is hereby corrected as shown below:

Col. 4, line 14, "to" should read -- a --. Col. 4, lines 40-41, delete ", E, F, G, H, and I". Col. 14, 35th item under heading "$R_2$" of Table, "$C_2H_9$" should read -- $C_2H_5$ --. Col. 20, line 53, "titainium" should read -- titanium --. Col. 21, line 37, "mixture or" should read -- mixture of --. Col. 22, line 35, "hydroxycarbonyl-phosphoric" should read -- hydroxycarbonylphosphonic --; line 39, "phorverbiindungen" should read -- phorverbindungen --; line 45, that portion of the formula reading "$R_{\overline{10}}$" should read -- $R_{10}$- --; line 60, the two portions of the formula reading "$R_{\overline{10}}$" should read -- $R_{10}$- --.

UNITED STATES PATENT AND TRADEMARK OFFICE
CERTIFICATE OF CORRECTION

PATENT NO. : 4,591,583

DATED : May 27, 1986

INVENTOR(S) : Ake J. E. Helgstrand et al

It is certified that error appears in the above-identified patent and that said Letters Patent is hereby corrected as shown below:

Col. 25, line 21, that portion of the formula reading

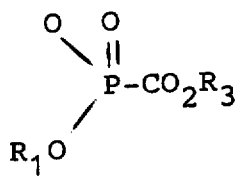

should read

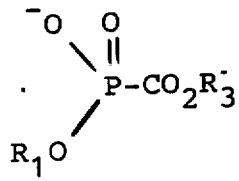

UNITED STATES PATENT AND TRADEMARK OFFICE
CERTIFICATE OF CORRECTION

PATENT NO. : 4,591,583

DATED : May 27, 1986

INVENTOR(S) : Ake J. E. Helgstrand et al

It is certified that error appears in the above-identified patent and that said Letters Patent is hereby corrected as shown below:

Col. 25, line 36, "I." should read -- L. --; line 40, that portion of the formula reading

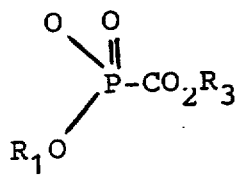

should read

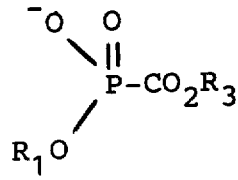

UNITED STATES PATENT AND TRADEMARK OFFICE
CERTIFICATE OF CORRECTION

PATENT NO. : 4,591,583

DATED : May 27, 1986

INVENTOR(S) : Ake J. E. Helgstrand et al

It is certified that error appears in the above-identified patent and that said Letters Patent is hereby corrected as shown below:

Col. 25, line 53, after "above" insert -- in A-H --. Col. 27, line 57, "is defined" should read -- is as defined --. Col. 30, line 39, "phosphosphites" should read -- phosphites --. Col. 35, line 56, "vauco" should read -- vacuo --. Col. 39, line 29, "vaper" should read -- vapor --. Col. 40, line 35, "molydate" should read -- molybdate --. Col. 42, end of line 44, "phoshonate" should read -- phosphonate --. Col. 49, line 65, "have" should read -- has --. Col. 55, line 19, "claim 7" should read -- claim 1 --.

Signed and Sealed this

Twenty-fourth Day of February, 1987

Attest:

DONALD J. QUIGG

*Attesting Officer*     *Commissioner of Patents and Trademarks*